United States Patent [19]

Lund

[11] 3,957,764
[45] May 18, 1976

[54] 6-AMINOPENICILLANIC ACID DERIVATIVES

[75] Inventor: Frantz Johannes Lund, Lyngby, Denmark

[73] Assignee: Lovens Kemiske Fabrik Produktionsaktieselskab, Ballerup, Denmark

[22] Filed: Nov. 6, 1972

[21] Appl. No.: 303,715

Related U.S. Application Data

[63] Continuation-in-part of Ser. No. 86,966, Nov. 4, 1970.

[30] Foreign Application Priority Data

Nov. 11, 1969 United Kingdom............... 55209/69
July 8, 1970 United Kingdom............... 33211/70

[52] U.S. Cl............................ 260/240 G; 260/239.1;
260/306.7 C; 424/270
[51] Int. Cl.²................ C07D 499/02; C07D 499/32
[58] Field of Search....... 260/239.1, 240 G, 306.7 C

[56] References Cited
UNITED STATES PATENTS

| | | | |
|---|---|---|---|
| 3,821,198 | 6/1974 | Lee et al...................... | 260/306.7 C |
| 3,855,233 | 12/1974 | Dolfini et al................. | 260/306.7 C |

OTHER PUBLICATIONS
Nature New Biology, Vol. 236, pp. 135–137, (1972).

*Primary Examiner*—Raymond V. Rush
*Assistant Examiner*—David E. Wheeler
*Attorney, Agent, or Firm*—Jackson, Jackson & Chovanes

[57] ABSTRACT

The invention relates to hitherto unknown derivatives of 6-aminopenicillanic acids of the formula

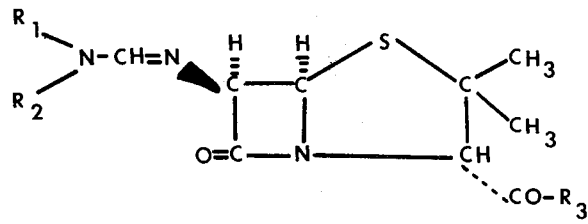

in which $R_1$ and $R_2$ are similar or different aliphatic, cycloaliphatic, aromatic or heterocyclic substituents linked directly or through alkyl groups to the nitrogen atom, or $R_1$ and $R_2$ together with the nitrogen atom form a heterocyclic ring, and $R_3$ is a hydroxyl or substituted hydroxyl group; to pharmaceutically acceptable salts, and to methods for producing these new compounds having a strong antibacterial effect, especially on gram-negative bacteria, to pharmaceutical preparations in dosage unit forms containing the compounds of the invention solely, or in synergistic mixtures with penicillins, and to methods of treating patients with the dosage units.

21 Claims, No Drawings

6-AMINOPENICILLANIC ACID DERIVATIVES

This application is a continuation-in-part of Ser. No. 86,966, filed Nov. 4, 1970.

This invention relates to hitherto unknown derivatives of 6-aminopenicillanic acid, to pharmaceutically acceptable salts thereof, to methods for the production of these new compounds, to pharmaceutical preparations in dosage unit forms containing the compounds of the invention solely, or in synergistic mixtures with penicillins, and to methods of treating patients with the dosage units.

The compounds of the invention are amidino-penicillanic acid derivatives of the formula:

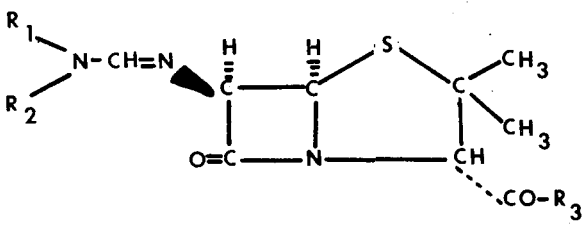

in which $R_1$ and $R_2$ represent the same or different substituents and each represents an aliphatic hydrocarbon radical, a mono- or bi-cyclic aryl radical, an aralkyl radical, a cycloalkyl radical, a cycloalkylalkyl radical, a heterocyclic radical or a heterocyclically substituted alkyl radical; or $R_1$ and $R_2$ when taken together with the nitrogen atom represent a ring system; and $R_3$ represents a hydroxyl group, or a substituted hydroxyl group.

More particularly, $R_1$ and $R_2$ represent an aliphatic hydrocarbon radical in which the carbon chain can be straight or branched, saturated or unsaturated, e.g. methyl, ethyl, propyl, isopropyl, butyl, sec.butyl, tert-.butyl, pentyl, hexyl, dodecyl, allyl, butenyl, pentenyl, or propargyl; a mono- or bicyclic aryl radical, e.g. a phenyl radical or a naphthyl radical; an aralkyl radical, such as mono- or bi-cyclic aralkyl radical, e.g. benzyl, phenylethyl, 1- or 2-naphthylmethyl; a cycloalkyl or cycloalkyl-alkyl radical, in which the cycloalkyl group can have from 3 to 10 ring members and can be saturated or have one or two double bonds, e.g. cyclopentyl, cyclohexyl, 1-adamantyl, 1-bi-cyclo(2.2.2)octyl, cyclopentenyl and cyclohexenyl, cyclopentylmethyl, cyclohexylmethyl, cyclopentenylethyl, cyclohexenyl-methyl, etc.; a heterocyclic radical or a heterocyclically substituted alkyl radical in which the heterocyclic part can be more or less hydrogenated and can have from 5 to 10 atoms in the ring and can contain oxygen, sulphur, or nitrogen atoms, e.g. pyridyl, pyrazinyl, pyrimidyl, pyrrolidyl, piperidyl, morpholinyl, thiazinyl furyl, thienyl, or quinolyl, in all of which the hetero atoms may be placed in any of the available positions; or $R_1$ and $R_2$ when taken together with the nitrogen atom represent heterocyclic radicals having from 5 to 10 atoms and optionally containing other hetero atoms in the ring, such as S, O or N, forming more or less hydrogenated ring systems e.g. piperidyl, morpholinyl, hexahydro-1H-azepin-1-yl, or hexahydro-1(2H)azocinnyl. The radicals $R_1$ and $R_2$ may be further substituted with halogen atoms, an alkyl, hydroxy, alkoxy or alkylthio group, an acyl group, a carboxy, carbalkoxy, carbamyl, carbamido, cyano or sulfonyl group, or an amino- or substituted amino group.

In particular, $R_3$ represents a hydroxyl group, or a substituted hydroxyl group $OR_4$, in which $R_4$ stands for an alkyl radical, an aryl radical, an aralkyl radical, a cycloalkyl-alkyl radical, an alkyl radical substituted with halogen, alkoxy, alkanoyl, aroyl, cyano, or a carbalkoxy group, e.g. methyl, ethyl, phenyl, benzyl, $\beta,\beta,\beta$-trichloroethyl, methoxymethyl, acetonyl, phenacyl, cyanomethyl, carbethoxymethyl, or dicarbethoxymethyl; or $R_4$ may represent an acyloxymethyl radical, the acyl part of which is an alicyclic, an aromatic, an ar-aliphatic or a heterocyclic acyl radical, such as acetyl, propionyl, butyryl, pivaloyl, cyclohexylacetyl, benzoyl, phenylacetyl, picolinyl, nicotinyl, furylacetyl, or thienylacetyl.

More specifically, preferred compounds of the invention are those of formula I in which $R_1$ and $R_2$ are selected from the group consisting of alkyl, chloroalkyl and hydroxy-alkyl having from 1 to 7 carbon atoms, alkoxyalkyl having from 2 to 7 carbon atoms, carbalkoxyalkyl having from 3 to 4 carbon atoms, cyanoalkyl and carbamylalkyl having from 2 to 3 carbon atoms, and allyl; phenyl; phenyl, chloro-phenyl, bromo-phenyl, phenoxy, carbobenzyloxy substituted methyl and ethyl radicals; cycloalkyl and cycloalkyl-methyl radicals having from 5 to 10 carbon atoms; methyl and ethyl radicals substituted with a heterocyclic ring selected from the group consisting of a 5-membered, unsaturated ring having as the hetero atom an oxygen or sulphur atom, and a 6-membered, unsaturated ring having as the hetero atom a nitrogen atom; and $R_1$ and $R_2$ form a straight or branched alkylene chain which together with the nitrogen atom form a saturated heterocyclic ring having from 4 to 8 carbon atoms; and $R_1$ and $R_2$ futhermore together with the nitrogen atom form a heterocyclic radical selected from the group consisting of morpholinyl-4, 4-methyl-piperazinyl-1, and 1,2,3,4-tetrahydro-isoquinolyl-2; and $R_2$ is hydroxyl; an alkoxy, chloroalkoxy, cyanoalkoxy, or phenylalkoxy radical, the alkoxy part of which has 1 to 4 carbon atoms; an alkanoyloxymethoxy radical having from 3 to 7 carbon atoms and a benzoyloxymethoxy radical; and pharmaceutically acceptable salts thereof.

The invention comprises all possible isomeric forms of the compounds of formula I, depending on the different subsitutents, whereas the 6-aminopenicillanic acid moiety has the configuration of that obtained by the fermentation process.

The compounds of the invention possess strong antibacterial effect, especially on gram-negative bacteria, and the toxicity is extremely low. This effect is quite unexpected, since of the hitherto known derivatives of 6-aminopenicillanic acid only those being substituted with an acyl group at the 6-amino group have shown an antibacterial effect. The effect on penicillin-sensitive, gram-positive bacteria is less than that of benzylpenicillin and of α-aminobenzylpenicillin, whereas the effect on gram-negative bacilli, e.g. coli and salmonella species, is on a many times higher level than that of e.g. benzylpenicillin and α-aminobenzylpenicillin. Table A below shows the antibacterial spectrum of 6-[(hexahydro-1H-azepin-1-yl)-methyleneamino]-penicillanic acid, hydrochloric, dihydrate (in the Table called FL 1060) as compared with α-aminobenzylpenicillin (ampicillin; abbr.: Amp.) and benzylpenicillin (in the Table called G-Pen). $IC_{50}$ means the concentration required for 50% inhibition.

Table A

| gram pos. and gram neg. strains: | FL 1060 | $IC_{50}$ (µg./ml.) Amp. | G-Pen. |
|---|---|---|---|
| Staph. aureus, penicillin sensitive | 5.0 | 0.025 | 0.016 |
| Staph. aureus, penicillinase producing | >100 | 130 | 100 |
| Diplococcus pneumoniae EA | 3.2 | 0.01 | 0.01 |
| Streptococcus pyogenes | 0.50 | 0.013 | 0.008 |
| Streptococcus faecalis E13 | >100 | 0.79 | 3.2 |
| Corynebacterium xerosis FF | 1.6 | | 0.013 |
| Listeria Monocytogenes FT | 50 | 0.10 | 0.10 |
| Erysipelothrix insidiosa FU | 20 | 0.040 | 0.025 |
| Bacillus subtilis KA2 | 5.0 | 0.025 | 0.010 |
| Bacillus megatherium KD | 0.50 | | 0.016 |
| Pseudomonas aeruginosa | >100 | >100 | >100 |
| Vibrio comma | 0.40 | 0.40 | 0.79 |
| Alcaligenes faecalis | 0.63 | 0.50 | 1.6 |
| Escherichia coli, average of 36 strains | 0.089 | 2.2 | 32 |
| Escherichia HA2 Leo strain | 0.016 | 2.0 | 32 |
| Klebsiella pneumoniae, average of 12 strains | 0.65 | 26 | 29 |
| Proteus, average of 8 strains | 0.23 | 1.3 | 5.4 |
| Salmonella paratyphi A | 0.13 | 0.4 | 3.2 |
| Salmonella schottmuelleri | 0.063 | 0.63 | 3.2 |
| Salmonella typhimurium | 0.063 | 0.50 | 2.5 |
| Salmonella abortivoequina | 0.040 | 0.25 | 2.5 |
| Salmonella hirschfeldii | 0.016 | 0.079 | 0.13 |
| Salmonella chlerasuis | 0.16 | 0.32 | 1.6 |
| Salmonella typhosa | 0.079 | 0.32 | 2.0 |
| Salmonella enteritidis | 0.16 | 0.40 | 2.5 |
| Shigella dysenteriae | 0.16 | 0.63 | 5.0 |
| Shigella flexneri | 0.050 | 0.79 | 10 |

In Table B below the activity of a number of the compounds of the invention against the Escherichia coli HA2 Leo strain of Table A is shown:

Table B

| Example No. | $R_1$ | $R_2$ | $R_3$ | $IC_{50}$ µg/ml |
|---|---|---|---|---|
| 16 | ethyl | ethyl | OH | 0.10 |
| 18 | ethyl | isopropyl | OH | 0.05 |
| 23 | methyl | cyclopentyl | OH | 0.05 |
| 24 | methyl | cyclohexyl | OH | 0.13 |
| 28 | methyl | benzyl | OH | 0.50 |
| | $R_1R_2N$- | | | |
| 37 | piperidyl-1 | | OH | 0.05 |
| 40 | 4-methyl-piperidyl-1 | | OH | 0.05 |
| 41 | 2,6-dimethyl-piperidyl-1 | | OH | 0.08 |
| 44 | hexahydro-1 (2H)-azocinnyl | | OH | 0.016 |

The compounds of Table B were obtained by enzymatic hydrolysis of the corresponding esters described in the Examples mentioned by treatment with a 20 per cent mouse serum at 37°C in 90 minutes.

Those in vitro experiments indicate activities up to 2000 times the activity of benzylpenicillin and 100 times the activity of α-amino-benzylpenicillin on coli bacteria, and for salmonella bacteria the corresponding figures are 50 times and 10 times, respectively.

The great difference between the spectrum of the hereinbefore mentioned FL 1060 and those of G-penicillin and ampicillin indicates a difference in the mode of action. This is also supported by in vivo experiments, in which mice (weight 27 to 30 g) were infected with 0.5 ml of a 24 hour old NIH bouillon culture of Escherichia Coli HA2 1000 times diluted in gastric mucin (5%) (Orthana). After half an hour and again after 6½ hours a single dose was given subcutaneously in 0.5 ml. of a 0.9 per cent sodium chloride solution. After 24 hours the numbers of surviving mice were registered.

All surviving mice were still alive after 4 days, when observation of them was terminated.

In the Table below the results of this experiment are shown:

Table C

| | Single dose µg | number of mice | per cent surviving |
|---|---|---|---|
| Control | | 10 | 0 |
| FL 1060 | 30 | 10 | 50 |
| | 15 | 10 | 0 |
| | 7.5 | 10 | 0 |
| Ampicillin | 300 | 10 | 70 |
| | 150 | 10 | 0 |
| | 75 | 10 | 0 |
| FL 1060 + Amp. | 15 + 150 | 10 | 100 |
| | 7.5 + 75 | 10 | 80 |
| | 3.75 + 37.5 | 10 | 0 |

The data of the table clearly shows a synergistic effect between 1060 and Ampicillin, and this fact is due to the surprising difference in the biological mode of action of the antibotics above.

It should be mentioned, however, that in animal experiments, the ratio of the amidino-penicillanic acid derivative to the penicillin in question may differ widely from the ratio mentioned above, the absorption rate and distribution in the body liquids of the antibiotic components contained in the composition being factors of importance to the choice of the appropriate ratio between the active ingredients.

The synergism above has been observed with various acyl-derivatives of 6-aminopenicillanic acid in admixture with the compounds of the invention, and it is also an object of the invention to provide such synergistic mixtures for clinical use.

It is also an object of the invention to provide methods for the preparation of the above described compounds of formula (I). In one method the compounds are prepared by reacting a reactive derivative of an amide or thioamide of the formula

(II)

in which $R_1$ and $R_2$ have the meanings defined before and $R_5$ stands for O or S, with a 6-aminopenicillanic acid derivative of the formula

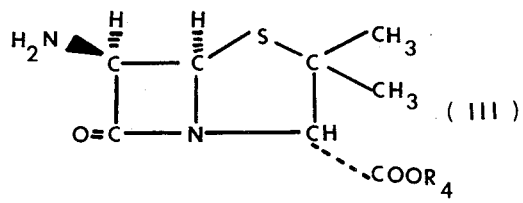
(III)

in which $R_4$ has the meaning defined before, or with a silyl ester of 6-aminopenicillanic acid. In the latter case the reaction must be followed by a solvolysis to provide the compounds of the invention in which $R_3$ is OH, which also may be obtained by cleavage of the other esters. Preferably, both reactions are carried out in solution in an inert solvent at or below room temperature.

The starting materials of formula II are known or can be prepared by methods known from generally used textbooks.

By well-known methods the amides of formula II can be transferred into reactive derivatives, such as acid amide halides, acid amide dialkyl sulphate complexes, or acid amide acetals. The preferred acid amide halides are the chlorides or bromides, and they can be prepared by treating the amides with halogenating agents. It is preferred to use halogenating agents which throughout the reaction form gaseous byproducts, such as phosgene, oxalyl halides, or thionyl halides, but also others may be used. The reaction can be performed in inert, dry, organic solvents, e.g. ether or toluene, in which in most cases the amide halide will be insoluble and from which it can be isolated by filtration after the reaction is completed. The acid amide halides are hygroscopic and rather unstable and are therefore preferably used in the next step without purification.

The acid amide dialkyl sulphate complexes can be prepared by treating the amides with dialkyl sulphate, preferably dimethyl sulphate, under well-known conditions. By treating the acid amide dialkyl sulphate complexes with sodium alkoxides, e.g. sodium methoxide, acid amide acetals of the formula

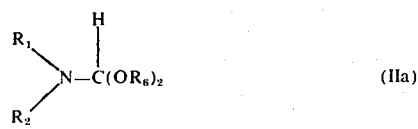
(IIa)

in which $R_1$ and $R_2$ have the meanings defined above and $R_6$ is an alkyl group, are formed, which acetals may also be used in the next step.

When acid thioamides are used as starting materials, a reactive derivative in form of an acid thioamide alkyl halide complex can be formed by treatment with alkyl halides, e.g. alkyl iodides. This reaction is well-known from the chemical literature.

The reaction conditions for the reaction between the amide derivative and the compound of formula III depend on the reaction components used in the process. When acid amide acetals are used in the reaction with the compound of formula III, the reaction temperature depends on the reaction components. The reaction is performed in inert organic solvents, for instance ether.

When acid amide halides, dialkyl sulphate complexes, or thioamide alkyl halide complexes are used, the reaction is performed in inert organic solvents, which are dry and free from traces of alcohols, preferably chloroform, in which the reaction components are soluble, but solvents in which the starting materials are insoluble, e.g. ether, may be used as well. The reaction is performed under cooling and in the presence of at least one equivalent of a tertiary amine, for example trimethylamine, triethylamine, N,N-diisopropylethylamine or N,N-diisopropylethylamine or N-methylmorpholine. If one equivalent of the tert.amine is used, the reaction product will be obtained as a salt when an acid amide halide is used, and as a $R_1,R_2$ -amidinopenicillanic acid derivative as such when the dialkyl sulphate complexes and thioamide alkyl halide complexes are used. When two or more equivalents of the tert. amine are used, a $R_1,R_2$-amidinopenicillanic acid derivative results which can be transformed to a salt, if desired.

The reaction time depends on the reactants, the temperature, and the solvents used in the process. When $R_3$ is hydroxyl, it is preferred to protect the carboxyl group as a trimethylsilyl ester or a dimethylsilyl diester which can easily be cleaved again after the reaction. The reaction is preferably performed with an acid amide acetal reactant. The preparation of the silyl esters of 6-aminopenicillanic acid is known from the literature. The silyl esters of the amidinopenicillanic acid are preferably cleaved by a hydrolysis or an alcoholysis under mild conditions not requiring the presence of any catalyst with acidic or alkaline properties.

In another method, the compounds of the invention can be prepared by reacting an amine of the formula $HNR_1R_2$ with a reactive derivative of a 6-formamidopenicillanic acid ester. Such a reactive derivative is for instance obtained by reacting a compound of formula III with a 1,1-dihalo-dimethyl ether, preferably 1,1-dichlorodimethyl ether, in the presence of a tertiary organic base. The reaction can be performed without isolation of the intermediate formed by the process, which in the example mentioned above is supposed to be a methoxymethylene derivative of the compound of formula III. The reactions are performed below or at room temperature and in the presence of an inert solvent, e.g. chloroform.

The reaction products of formula I can be purified and isolated in usual manner and may be obtained either in the free state or in the form of a salt. The free acid ($R_3$=OH) can also be obtained from some of the esters by an enzymatic hydrolysis or a mild hydrogenolysis, and if the free acid is the reaction product, the esters can be prepared therefrom by methods known from the literature.

The compounds of formula III are partly known compounds and may be prepared by esterification of 6-aminopenicillanic acid or a protected 6-aminopenicillanic acid, such as the 6-trityl derivative thereof. The trityl group may be split off after the reaction under conditions not affecting the lactam ring. They can also be prepared by esterification of the generally industrially used penicillins, whereafter the acyl side chain can be split off chemically or enzymatically under such conditions that the ester group is not affected.

ymethyl esters can preferably be alkanoyloxymethyl esters prepared from alkanoic acids, such as acetic, propionic, butyric, valeric, caproic, trimethylacetic or diethylacetic acid. These esters are hydrolyzed under the influence of enzymes present in blood and tissues to the corresponding free acids of formula I, which generally have a more pronounced antibacterial activity than the esters.

Such favourable high blood levels have been demonstrated e.g. after oral administration of a single dose of 200 mg of pivaloyloxymethyl 6-[(hexahydro-1H-azepin-1-yl)-methyleneamino]-penicillanate hydrochloride in 200 ml water to 4 fasting persons as will appear from Table D, in which the figures show the serum concentrations in $\mu$g/ml of the corresponding acid.

Table D

| Person | $\mu$g per ml serum | | | | | Urinary excretion in per cent of administered dose | | |
|---|---|---|---|---|---|---|---|---|
| | Hours | | | | | | | |
| | 1/4 | 1/2 | 1 | 2 | 4 | 0–6 | 6–24 | 0–24 |
| DR | 3.2 | 6.4 | 4.2 | 1.7 | 0.34 | 43 | 6.6 | 50 |
| GK | 2.1 | 3.8 | 4.2 | 2.0 | 0.29 | 53 | 2.7 | 56 |
| BB | 2.1 | 3.8 | 3.5 | 1.6 | 0.42 | 55 | 0.81 | 56 |
| LT | 2.1 | 5.1 | 3.3 | 1.3 | 0.34 | 45 | 1.1 | 46 |

The compound of formula I may be isolated as such or in the forms of salts with pharmaceutically acceptable salts, such as hydrochloric acid, phosphoric acid, nitric acid, p-toluenesulfonic acid, acetic acid, propionic acid, citric acid, tartaric acid, or maleic acid. When $R_3$ stands for a hydroxyl group, the compounds of formula I may be isolated as the amphoion (zwitterion) or as a salt, e.g. the alkali metal salts and the ammonium or amine salts, or salts with strong acids.

Such salts may also be produced from other antibiotics with acidic or basic characteristics, e.g. fusidic acid, and in particular with acidic antibiotics with which the present compounds form synergistic mixtures, such as penicillins. Acids which results in salts with the compounds of the invention having desirable properties with a view to absorption and use in clinical practice are especially useful. Examples of such salts are the pamoate or the naphsylate, or salts which contain probenecid, the latter compound delaying the excretion of the compounds of the invention resulting in prolonged blood levels.

For certain medical purposes it will be advantageous to use the compounds of the invention either in the form of the free acids or of their salts, and this will apply in particular for parenteral treatment.

Thus, in the case where $R_3$ is a hydroxyl group, the compounds are advantageous administered by injection of an aqueous, sterile solution or suspension of an appropriate salt.

For oral administration it will be more favourable to use the easily hydrolyzable esters of formula I, such as acyloxymethyl esters or cyanomethyl esters which, chemically or enzymatically will be rapidly hydrolyzed to the corresponding free acids in the body. In other cases, less hydrolyzable esters will be preferred in order to obtain a prolonged blood level and/or a particular distribution in the body fluids.

In particular, however, some acyloxymethyl esters are advantageous in being absorbed more efficiently after oral administration than the corresponding free acids, thereby causing high blood levels. Such acylox- The invention furthermore concerns therapeutical compositions adapted for use in the treatment of infectious diseases. The compositions of the invention contain as the therapeutically active component or components primarily one or more members of the class consisting of compounds of formula I and its salts with atoxic pharmaceutically acceptable bases and acids, mixed up with solid or liquid pharmaceutical carriers and auxiliary agents. Furthermore the composition can contain other therapeutically active ingredients with a view to combatting bacterial infections, and in particular the compositions of the invention contain known penicillins in synergistic mixtures with compounds of formula I.

In the compositions, the proportion of therapeutically active material to carrier substance and auxiliary agent can vary between 1% and 99%. The compositions can either be worked up to pharmaceutical forms of presentation such as tablets, pills or dragees, or can be filled in medical containers such as capsules, or as far as mixtures are concerned filled into bottles. The total amount of active ingredients in the composition lies preferably in the range from 10 per cent to 90 per cent of the composition in the case of this being in solid form and intended for oral administration and preferably from 0.5 to 30 per cent in the case of the composition being in a liquid form intended for injection. Pharmaceutical organic or inorganic solid or liquid carriers suitable for oral, enteral or topical administration can be used to make up the composition. Gelatine, lactose, starch, magnesium stearate, talc, vegetable and animal fats and oils, gum, polyalkylene glycol, or other known carriers for medicaments are all suitable as carriers. Furthermore, the compositions may contain other pharmaceutically active components which can appropriately be administered together with the compounds of the invention in the treatment of infectious diseases, such as other suitable antibiotics.

Another object of the invention resides in the selection of a dose of the compounds of formula I and a dosage unit which can be administered so that the desired activity is achieved without simultaneous secondary effects.

By the term "dosage unit" is meant a unitary, i.e. a single dose capable of being administered to a patient, and which may be readily handled and packed, remaining as a physically stable unit dose, comprising either the active material as such or a mixture of it with a solid pharmaceutical carrier.

As mentioned before, the toxicity of the compounds is very low which is for instance reflected in an animal experiment where 600 mg/kg of pivaloyloxymethyl 6-[(hexahydro-1H-azepin-1-yl)-methyleneamino]-penicillanate were given orally to rats for 55 days and 200 mg/kg of the same compound were given orally to dogs for 47 days, without toxic symptoms being observed on macroscopic, biochemical or haematological examinations.

In preliminary clinical trials it has been found that the compounds of formula I as the sole active ingredient are conveniently administered in dosage units containing not less substance than corresponding to from 0.025 g to 1 g of the free acid of formula I ($R_3$=OH) and preferably to from 0.05 g to 0.5 g. For parenteral treatment the compounds of formula I are conveniently administered in doses from 0.1 g to 1 g, calculated as the free acid and employed as the free acid or one of its atoxic salts dissolved or suspended in a fluid vehicle suitable for injection.

Such dosage units are conveniently administered once, twice or three times a day at appropriate intervals, always, however, with the physicians prescription and depending on the condition of the patient. Accordingly the daily dose will amount to from 0.1 g to 5.0 g of the compound of formula I as the sole active ingredient calculated as free acid, and preferably from 0.1 g to 2 g per day.

Such a daily dose may also be administered orally in the form of an aqueous or oily suspension or solution, and preferably aqueous suspension, of the compound of formula I in the form of an easily hydrolyzable ester e.g. the pivaloyloxymethyl ester for which purpose appropriately is employed a therapeutical composition as described above and containing from 10 mg to 50 mg calculated as the free acid of such compound of formula I per ml of the fluid vehicle.

It is still another object of the invention to provide a therapeutical composition in dosage unit form which contains besides a compound of formula I a penicillin resulting in a synergistic activity.

Suitable penicillins in the synergistic mixture can be known natural, biosynthetic and semi-synthetic penicillins, and in particular penicillins in which the side chain contains for instance the following radicals: a substituted or unsubstituted benzyl radical such as an $\alpha$-phenoxybenzyl radical; a 2,6-dimethoxyphenyl radical; $\alpha$-substituted benzyl, 1,4-cyclohexadienylmethyl or 1-cyclohexenylmethyl radicals, such as $\alpha$-hydroxy, $\alpha$-azido, $\alpha$-amino, $\alpha$-carboxy, $\alpha$-sulfo or $\alpha$-sulfoaminobenzyl, 1,4-cyclohexadienylmethyl or 1-cyclohexenylmethyl radicals; an $\alpha$-amino-p-hydroxybenzyl radical; an $\alpha$-phenoxyalkyl radical such as an $\alpha$-phenoxymethyl, $\alpha$-phenoxyethyl or $\alpha$-phenoxypropyl radical; a $\beta$-amino-$\alpha$-phenyl-ethyl radical; an unsubstituted or substituted isoxazolyl radical, such as the 3-phenyl-5-methyl-4-isoxazolyl, 3-(2-chlorophenyl)-5-methyl-4-isoxazolyl, 3-(2,6-dichlorophenyl)-5-methyl-4-isoxazolyl, 3-(2-chloro-6-fluorophenyl)-5-methyl-4-isoxazolyl radicals; a 2-ethoxy-1-naphthyl radical; a 3-carboxy-2-quinoxalyl radical; and an $\alpha$-(3-guanyl-1-ureido)-benzyl radical.

In the therapeutical composition of the invention the penicillins may be present as their known water-insoluble or water-soluble salts, and some of the free penicillins may be used as such, for instance the penicillin V acid, or as an amphoion, e.g. ampicillin.

As usable salts of the penicillins mention may be made of the water-soluble sodium, potassium, ammonium, triethylamine, piperidine, morpholine, cyclohexylamine, and mono- and diethanol amine salts, and the slightly water-soluble calcium, magnesium, dibenzylethylenediamine, benzyl-$\beta$-phenylethylamine, and procaine salts or salts with other antibiotics with acidic or basic characteristics.

As is well known, administration by the oral route is preferred, and it may therefore be convenient to combine one of the penicillins suitable for oral administration with one of the compounds of formula I also suitable for oral administration. Thus one or more of the above compounds are appropriately employed as their acyloxymethyl esters, of which by way of example mention may especially be made of the alkanoyloxymethyl esters of $\alpha$-amino-benzylpenicillin, e.g. the pivaloyloxymethylester. Such acyloxymethyl esters are known from e.g. U.S. Pat. No. 3,697,507 and No. 3,250,679 or they can be prepared in analogy to the known esters.

The synergistic composition according to the invention can be worked up to any pharmaceutical forms of presentation such as tablets, pills, dragees, or suppositories, or the composition can be filled into medical containers such as capsules or ampoules or, as far as mixtures or ointments are concerned, they may be filled into bottles, tubes, or similar containers.

If the synergistic composition and dosge units thereof are intended to be used for parenteral administration the compounds of formula I contained therein are those in which $R_3$ is a hydroxyl group, the compounds being employed as a suitable atoxic salt or as the amphoion, and correspondingly the penicillin employed is employed in the form of one of its salts, or its amphoion, if any.

On the other hand, if the composition and dosage units thereof are intended to be used for oral administration the compounds of formula I are as mentioned before preferably employed as their acyloxymethyl esters admixed with a penicillin, one of its salts, or one of its acyloxymethyl esters.

In such synergistic compositions of the invention the compound of formula I is present in an amount of from 20 to 80 per cent calculated on the basis of the total amount of antibiotically active components in the form of their free acids forming the synergistic mixture.

In the treatment of patients suffering from infectious diseases the synergistic compositions of the invention are conveniently administered in daily doses from 0.2 g to 4 g, corresponding to the amount of compound of formula I plus the penicillin derivative in question calculated as free acids, but present as such or as salts or easily hydrolyzable esters thereof.

Appropriately, the daily dose is given in the form of dosage units, e.g. tablets, of which 1–2 tablets are given 2–4 times a day.

Such dosage units can according to the invention contain from 0.1 g to 0.8 g in total of the compound of formula I and the penicillin derivative in question calculated as free acids, but present as such or as salts or easily hydrolyzable esters thereof.

As an example of a dosage unit, mention may be made of tablets containing each 175 mg of pivaloyloxymethyl α-amino-benzyl-penicillinate, hydrochloride and 150 mg of pivaloyloxymethyl 6-[(hexahydro-1H-azepin-1-yl)-methyleneamino]-penicillanate, hydrochloride together with the necessary carrier and/or auxiliary agents.

It shall be understood, however, that the adequate doses and frequency of administration may vary, depending upon the condition of the patient and the character of the infection, and shall be determined by the medical practitioner.

In clinical trials 46 patients suffering from bacterial infections in the urinary system, have been treated with pivaloyloxymethyl α-amino-benzyl penicillinate hydrochloride, with pivaloyloxymethyl 6[(hexahydro-1H-azepin-1-yl)-methyleneamino]-penicillanate hydrochloride and with mixtures of these two compounds in various ratios from 0.5 to 2.5. In the groups of patients treated with the above mixtures, the results showed a clear synergistic effect.

The dosage unit of the invention may also contain other components which may contribute to increasing the scope of utility of the composition contained in the dosage unit in question, e.g. antibacterially active cephalosporins, sulfonamides or nitro-furan derivatives, or sulfamylbenzoic acid derivatives which are capable of delaying the excretion of the components administered.

Furthermore, according to the invention the dosage unit can appropriately be in the form of tablets, the inner core of which contains one or more of the active components with the necessary pharmaceutical auxiliary agents, whereas the outer core contains the other active component(s) together with adequate auxiliary agents, or such double tablets are provided in which the halves contain their respective component(s) under conditions where no interaction between the components can occur.

The invention will now be illustrated by the following, non-limiting Examples.

EXAMPLE 1

Pivaloyloxymethyl
6-[(hexahydro-1H-azepin-1-yl)-methyleneamino]-penicillanate 12.7 g of N-formylhexamethyleneimine were dissolved in 250 ml of dry ether. While stirring and cooling, 8.5 ml of oxalyl chloride in 50 ml of dry ether were added dropwise. The mixture was stirred overnight at room temperature. The precipitated amide chloride was filtered off and washed with dry ether, and was placed in an exsiccator.

27.5 g of pivaloyloxymethyl 6-aminopenicillanate tosylate were suspended in 1500 ml of ethyl acetate under continuous stirring and cooling in an ice bath. 950 ml of ice-cold aqueous sodium bicarbonate (2 per cent) were added. The ethyl acetate layer was separated and was shaken with 750 ml of ice-water containing 25 ml of aqueous sodium bicarbonate (2 per cent), after which it was dried over magnesium sulfate at 0°C. After filtration, the solution was evaporated to dryness in vacuo. The residue was dissolved in a solution of 15.5 ml of dry triethylamine in 75 ml of dry alcohol-free chloroform. To this solution 10 g of the above prepared amide chloride dissolved in 75 ml of dry alcohol-free chloroform were added dropwise at a temperature of about −20°C. After standing for half an hour at −20°C, the temperature was raised to 0°C within 15 minutes. The solution was evaporated to dryness in vacuo. The residue was stirred with 750 ml of ether. Undissolved triethylamine hydrochloride was filtered off, and the filtrate was again evaporated to dryness in vacuo. The residue was reprecipitated from acetone (200 ml) - water (150 ml). After recrystallization from cyclohexane, an analytically pure product was obtained with a melting point of 118.5°–119.5°C and $[\alpha]_D^{20} : + 231°$ (c=1, 96% ethanol).

The starting material, N-formylhexamethyleneimine, was prepared from hexamethyleneimine and chloral and had a boiling point of 111°–112°C / 10 mm $H_g$.

EXAMPLE 2

Pivaloyloxymethyl
6-(N,N-dimethylformamidino-N')-penicillinate hydrochloride 5.8 g of chlorodimethylformiminium chloride were dissolved in 40 ml of dry alcohol-free chloroform. At a temperature of −30°C to −40°C this solution was added dropwise to a solution of 13.3 g of pivaloyloxymethyl 6-aminopenicillanate and 12.4 ml of triethylamine in 75 ml of dry, alcohol-free chloroform while stirring. The temperature was raised to 0°C within 1 hour. The solution was evaporated in vacuo, and the residue was treated with 200 ml of dry ether. After filtration from triethylamine hydrochloride the filtrate was evaporated in vacuo. The oily residue was dissolved in 40 ml of isopropanol. At 0°C and while stirring, 4 ml of a solution of dry hydrogen chloride in isopropanol (9N) were added dropwise. Then 150 ml of ether were added. After filtration, washing with ether, and recrystallization from acetone-ether, the compound was obtained in analytically pure form having a melting point of 146°C. $[\alpha]_D^{20} : + 209°$ (c=1, 96% $C_2H_5OH$).

EXAMPLE 3

Pivaloyloxymethyl
6-[(hexahydro-1H-azepin-1-yl)-methyleneamino]-penicillanate

To a solution of pivaloyloxymethyl 6-aminopenicillanate (3.3 g) and triethylamine (2.8 ml) in dry chloroform (35 ml) was added 1,1-dichlorodimethyl ether (1.1 g) at 0°C. After 20 hours at room temperature, hexamethyleneimine (1.1 ml) was added, and the solution was kept at 0°C overnight. The solution was evaporated in vacuo, and the residue was triturated with water (75 ml). The aqueous phase was removed by decantation. The residue was dissolved in diluted hydrochloric acid (pH about 3) and filtered. The filtrate was made alkaline with sodium bicarbonate (pH about 7.5). The precipitate was sucked off and was washed with water to yield a product with a melting point of 117°–119°C. The IR spectrum was identical with that of an authentic sample.

EXAMPLE 4

Cyanomethyl
6-(N,N-diethylformamidino-N')-penicillanate oxalate

A. Cyanomethyl 6-aminopenicillanate p-toluenesulfonate

To a stirred suspension of 6-aminopenicillanic acid (43.3 g) in dimethylformamide (400 ml) at room temperature was added triethylamine (35 ml) and chloroacetonitrile (25.5 ml). Stirring was continued at room temperature for 24 hours. The mixture was diluted with 400 ml of ethyl acetate, and filtered. The solid was washed with ethyl acetate. The filtrate was diluted with 800 ml of ethyl acetate, extracted four times with 200 ml of water, and dried over magnesium sulfate. After filtration, an 0.5 M solution of p-toluenesulfonic acid in ethyl acetate (320 ml) was added with stirring. The precipitate was filtered off and washed with ethyl acetate and ether. Recrystallization from methanol-ethyl acetate afforded a colourless analytically pure product, melting at 154.5°–156°C (dec.). $[\alpha]_D^{20}: +146°$ (c=1, 96% $C_2H_5OH$).

B. Chlorodiethylformiminium chloride 1.7 ml of oxalyl chloride dissolved in 10 ml of dry ether were slowly added to a solution of 2.2 ml of diethylformamide in 50 ml of dry ether at 0°C with stirring. After stirring at room temperature for three-fourths hour, the precipitate was quickly filtered with suction, washed with dry ether, and stored in an exsiccator.

C. Cyanomethyl 6-(N,N-diethylformamidino-N')-penicillanate oxalate

Cyanomethyl 6-aminopenicillanate was liberated from 4.7 g of the p-toluenesulfonate according to the procedure of Example 1 and dissolved in 15 ml of dry, alcohol-free chloroform. Dry triethylamine (3.1 ml) was added, and the solution was cooled to −30°C. A solution of 1.7 g of crude amide chloride in 15 ml of dry, alcohol-free chloroform was slowly added at −20°C to −30°C, with stirring. In the course of three-fourths hour the temperature was allowed to raise to 0°C. The solution was evaporated in vacuo, and the residue was triturated with 200 ml of ether. After filtration and evaporation in vacuo of the filtrate, the residue was dissolved in 200 ml of ether and treated with "Dicalite" filter aid (diatomaceous earth). A solution of 0.85 g of anhydrous oxalic acid in 50 ml of ether was slowly added to the filtrate with stirring. When the precipitate had settled, the supernatant liquor was decanted, and the precipitate was stirred with fresh ether. After filtration, the product was recrystallized twice from acetone-ether to yield the analytically pure material melting at 121°–122.5°C. $[\alpha]_D^{20}: +214°$ (c=1, 96% $C_2H_5OH$).

EXAMPLE 5

γ-Phenylpropyl 6-[(hexahydro-1H-azepin-1-yl)-methyleneamino]-penicillanate hydrochloride A. γ-Phenylpropyl 6-aminopenicillanate To a stirred suspension of 6-aminopenicillanic acid (21.6 g) in dimethylformamide (200 ml), triethylamine (11.4 ml) and γ-bromophenylpropane (22.0 g) were added at room temperature. Stirring was continued at room temperature for 18 hours. 200 ml of ethyl acetate were added, and the mixture was filtered. The filtrate was diluted with 400 ml of ethyl acetate, extracted four times with 100 ml of water and dried over magnesium sulfate. After evaporation in vacuo, the oily residue was dissolved in a mixture of water and ether (200 ml of each) with stirring and ice-cooling. By slow addition of diluted hydrochloric acid the pH was adjusted to 3 to 4. The aqueous phase was separated, made alkaline to a pH of about 7.5 by addition of sodium bicarbonate, and extracted with ether. After drying, the ether was evaporated in vacuo to leave the crude ester as an oil.

B. γ-Phenylpropyl 6-[(hexahydro-1H-azepin-1-yl)-methyleneamino]-penicillanate hydrochloride 2.2 g of the crude ester and 2.0 ml of dry triethylamine were dissolved in 15 ml of dry, alcohol-free chloroform and cooled to −60°C with stirring. A solution of 1.2 g of the amide chloride of Example 1 in 10 ml of dry, alcoholfree chloroform was slowly added. The temperature was raised to 0°C during 1 hour, after which the solution was evaporated in vacuo. After trituration with 80 ml of ether, the solid formed was filtered off. The filtrate was extracted with 80 ml of water with stirring and ice-cooling, while the pH of the aqueous phase was lowered to about 3. The aqueous phase was separated, made alkaline with sodium bicarbonate, and extracted with ether. After drying, the ether was evaporated in vacuo. The oily residue was dissolved in 10 ml of isopropanol and treated with 0.35 ml of a solution of dry hydrogen chloride in isopropanol (9N), with stirring and ice-cooling. The precipitate was filtered off and washed with a little isopropanol. Two recrystallizations from methanol-ether yielded an analytically pure product melting at 163.5°C. $[\alpha]_D^{20}: +201$ (c=1, 96% $C_2H_5OH$).

EXAMPLE 6

6-[(Hexahydro-1H-azepin-1-yl)-methyleneamino]-penicillanic acid.

A solution of the amide chloride of Example 1 (4.6 g) in dry, alcohol-free chloroform (20 ml) was added slowly to a solution of trimethylsilyl 6-aminopenicillanate (7.2 g) and triethylamine (3.5 ml) in dry, alcohol-free chloroform (50 ml) with stirring and cooling to −70°C. The temperature was raised to 0°C during 1½ hours. The solution was evaporated to dryness in vacuo, and the residue was triturated with dry ether (200 ml). The precipitate was filtered off and washed with dry ether. The filtrate was diluted with ether (200 ml). 2-Butanol (2.8 ml) was added dropwise with stirring and cooling to 0°C. The stirring was continued for 1/4 hour at 0°C, after which the precipitate was filtered off, washed with ether, and dried. It was a white, amorphous powder, soluble in water. Paper chromatography was performed using the descending technique on Whatman No. 1 paper with the solvent system n-butanol-ethanol-water (4:1:5). The $R_f$ value was 0.5.

| NMR spectrum ($D_2O$): | | | |
|---|---|---|---|
| $C_{(2)}(CH_3)_2$ | 3 H | s | at 1.58 |
|  | 3 H | s | at 1.71 |
| $(CH_2)_4$ | 8 H | m | at 1.4–2.0 |
| $N(CH_2)_2$ | 4 H | m | at 3.45–3.90 |
| $C_{(3)}H$ | 1 H | s | at 4.34 |
| $C_{(5)}H$ | 1 H | d | at 5.62 (J=4.0) |
| $C_{(6)}H$ | 1 H | d | at 5.47 (J=4.0) |
| N—CH=N | 1 H | broad s | at 8.03 |

The chemical shifts are given as ppm in δ values with sodium 2.2.3.3-tetradeutero-3-trimethylsilylpropionate (0 ppm) as internal standard. Coupling constants (J) are in cps.

EXAMPLE 7

Butyl 6-(N,N-diethylformamidino-N')-penicillanate hydrochloride

A. Butyl 6-aminopenicillanate tosylate

To a stirred suspension of 6-aminopenicillanic acid (21.7 g) in dimethylformamide (200 ml) at room temperature was added triethylamine (16.8 ml), n-butyl bromide (21.4 ml), and a catalytic amount of triethylammonium iodide. Stirring was continued at room temperature for 24 hours. Ethyl acetate (200 ml) was added, and the mixture was filtered. The solid was washed with ethyl acetate. The filtrate was diluted with ethyl acetate (400 ml), extracted four times with water (100 ml), and dried over magnesium sulfate. After eveporation in vacuo, the reddish oil was dissolved in water (250 ml) with stirring and ice-cooling, the pH being adjusted to 3.5 by slow addition of diluted hydrochloric acid. The aqueous phase was separated, filtered, made alkaline to a pH of 7.5 by addition of sodium bicarbonate, and extracted with ether (200 ml). After drying over magnesium sulfate, the ethereal phase was treated with a solution of p-toluenesulfonic acid (9.5 g) in ether (250 ml) with cooling and stirring. The precipitate was filtered off and washed with ether. The melting point of the crude product was 139°–140°C.

B. Butyl 6-(N,N-diethylformamidino-N')-penicillanate hydrochloride

Butyl 6-aminopenicillanate was liberated from 4.9 g of the tosylate, according to the procedure of Example 1 for pivaloyloxymethyl 6-amino-penicillanate tosylate, and dissolved in 15 ml of dry, alcohol-free chloroform. Dry triethylamine (3.1 ml) was added, and the solution was cooled to −30°C. A solution of chlorodiethylformiminium chloride (1.7 g) in chloroform (15 ml) was slowly added at −20°C to −30°C with stirring. In the course of three-fourths hour the temperature was raised to 0°C. The solution as evaporated in vacuo, and the residue was triturated with ether (200 ml). The triethylammonium chloride formed was filtered off, and the filtrate was evaporated in vacuo. The residue was dissolved in water (200 ml) by addition of diluted hydrochloric acid until a pH of about 3.5. After filtration with Dicalite filter aid, the pH was brought to 7.5 by addition of sodium bicarbonate. The oily phase was extracted with ether (200 ml), dried, and evaporated in vacuo. To the residue in isopropanol (10 ml) was added 1 ml of dry hydrogen chloride in isopropanol (8.5 N) with cooling and stirring. Addition of ether (150 ml) precipitated the hydrochloride with a melting point of 126°–130°C. After recrystallizations from acetone-ether and isopropanol-ether the compound was obtained in analytically pure form having a melting point of 140.5°–141°C. $[\alpha]_D^{20}$ : + 241° (c=1, 96% $C_2H_5OH$).

EXAMPLE 8

Pivaloyloxymethyl 6-(N,N-dimethylformamidino-N')-penicillanate hydrochloride

A solution of pivaloyloxymethyl 6-aminopenicillanate (3.3 g) and 1,1-dimethoxy-trimethylamine (1.2 g) in ether (30 ml) was slowly evaporated at room temperature (1 hour) and thereafter at 40°C (3 hours). The oily residue was dissolved in diluted hydrochloric acid (pH about 3), filtered and the filtrate treated with sodium bicarbonate (pH about 7.5). The liberated base was taken up in ether, which was dried and evaporated. To the oily residue dissolved in isopropanol (10 ml) was added 0.36 ml of dry hydrogen chloride (8.5 N) in isopropanol and thereupon ether (100 ml). The precipitate had a melting point of 130°–144°C. A recrystallization from acetone-ether raised the melting point to 143°–146°C. The IR spectrum was identical with that of an authentic sample.

EXAMPLE 9

Pivaloyloxymethyl 6-[(hexahydro-1H-azepin-1-yl)-methyleneamino]-penicillanate

To a solution of pivaloyloxymethyl 6-aminopenicillanate (3.3 g) and N,N-diisopropylethylamine (1.7 ml) in dry chloroform (35 ml) at 0°C was added 2.5 g of the N-formylhexamethyleneimine-dimethyl sulfate complex prepared according to the method of Bredereck et al. (Chem.Ber. 101, 41 (1968)). After 20 hours at 0°–5°C, the solution was evaporated, and the residue was crystallized from acetone-water yielding a product with a melting point of 115°–117°C. The IR spectrum was identical with that of an authentic sample.

EXAMPLE 10

Pivaloyloxymethyl 6-[(hexahydro-1H-azepin-1-yl)-methyleneamino]-penicillanate hydrochloride The free base of Example 9 (36 g) was suspended in isopropanol (165 ml) with stirring and ice-cooling. 9.7 ml of a solution of dry hydrogen chloride (8.5 N) in isoopropanol were added. From the resulting solution the hydrochloride did crystallize spontaneously. Ether (350 ml) was added. After filtration and recrystallization from methanol-diisopropyl ether, an analytically pure product was obtained with a melting point of 172°–173°C. $[\alpha]_D^{20}$ : + 219° (c=1, 0.1 N HCl).

EXAMPLE 11

Pivaloyloxymethyl 6-[(hexahydro-1H-azepin-1-yl)-methyleneamino]-penicillanate hydroiodide To a solution of the above mentioned hydrochloride (2.6 g) in 15 ml of water was added sodium iodide (0.8 g) in water (5 ml). The precipitate was sucked off, washed with water, and dried. After recrystallizations from isopropanol-ether and ethanol-ether, the analytically pure product had a melting point of 153°–154°C. $[\alpha]_D^{20}$ : + 182° (c=1, 96% $C_2H_5OH$).

EXAMPLE 12

β,β,β-Trichloroethyl 6-[(hexahydro-1H-azepin-1-yl)-methyleneamino]-penicillanate A. β,β,β-Trichloroethyl 6-aminopenicillanate hydrochloride To a solution of phosphorus pentachloride (11.1 g) in dry, alcohol-free chloroform (110 ml) was added quinoline (12 ml) with stirring. At −20°C β,β,β-trichloroethyl benzylpenicillinate (14.8 g) was added. The stirring was continued at −15°C for 20 minutes. At −40°C n-propanol (37 ml) was added during 2–3 minutes. The temperature rose to −15°C and was kept there for 15 minutes. The solution was poured onto a mixture of petroleum ether (330 ml), saturated aqueous sodium chloride (88 ml) and water (16 ml), while stirring and cooling with ice-water. The mixture was seeded and stirred for 30 minutes. The aqueous phase was removed, and the precipitate in the organic phase was isolated by filtration. After washing with a little isopropanol and with ether, the compound had $[\alpha]_D^{20}$ : + 153° (c=1, 0.1 N HCl). The analytically pure compound was obtained by liberating the free base with sodium bicarbonate and reprecipitating the salt with hydrogen chloride in isopropanol. After recrystallization from ethanol-ether it had a melting point of 153.5°–155.5°C. $[\alpha]_D^{20}$ : + 160° (c=1, 0.1 N HCl).

B. β,β,β-Trichloroethyl 6-[(hexahydro-1H-azepin-1-yl)-methylene-amino]-penicillanate A solution of the amide chloride of Example 1 (1.0 g) in pure chloroform (15 ml) was added slowly to a solution of the above prepared crude ester (1.9 g) and triethylamine (2.2 ml) in pure chloroform (15 ml) at −20°C with stirring. The temperature was raised to 0°C during 45 minutes, after which the solution was evaporated in vacuo. The residue was triturated with ether (100 ml), and the solid formed was filtered off. The filtrate was evaporated in vacuo, and the oily residue was triturated with water (50 ml). The solid was isolated by filtration and recrystallized from acetone-water and isopropanol-water yielding an analytically pure product with a melting point of 99°–101°C. $[\alpha]_D^{20}$ : + 214° (c=1, 96% $C_2H_5OH$).

EXAMPLE 13

6-(N,N-Di-n-butylformamidino-N′)-penicillanic acid hydrate

A solution of N-(dimethoxymethyl)-dibutylamine (4.9 g) in dry ether (100 ml) was slowly added to a solution of trimethylsilyl 6-aminopenicillanate (7.0 g) in ether (500 ml) at −30°C with stirring. The temperature was raised to 0°C during half an hour. Water (25 ml) was added during 10 minutes. The aqueous phase was separated, and the ethereal phase was extracted with 25 ml of water. The combined aqueous phases were freeze-dried. The solid product thus obtained was triturated with water (10 ml) at 0°C, filtered, and air-dried. It melted with decomposition at 106°C and was analytically pure. $[\alpha]_D^{20}$ : + 261° (c=1, 0.1 N HCl).

EXAMPLE 14

6-[(Hexahydro-1H-azepin-1-yl)-methyleneamino]-penicillanic acid hydrochloride dihydrate A solution of benzyl 6-[(hexahydro-1H-azepin-1-yl)-methyleneamino]-penicillanate hydrochloride (4.3 g) (Ex.42) in methanol (70 ml) was hydrogenated with palladium on charcoal catalyst (10%, 4.3 g) at room temperature and under one atmosphere of hydrogen for 21 minutes. After filtration of the catalyst, the filtrate was evaporated in vacuo. The oily residue was dissolved in 95% isopropanol (28 ml). After filtration with Dicalite filter aid and washing with isopropanol (15 ml), diisopropyl ether (50 ml) was added. The precipitate was filtered off, washed with diisopropyl ether, and air-dried. The melting point was 87°–89°C (dec.). $[\alpha]_D^{20}$ : + 238° (c=1, $H_2O$).

EXAMPLE 15

Pivaloyloxymethyl 6-[(hexahydro-1H-azepin-1-yl)-methyleneamino]-penicillanate

A. Methyl iodide complex of N-thioformylhexamethyleneimine

To a solution of N-thioformylhexamethyleneimine (2.9 g) in dry ether (10 ml) was added methyl iodide (1.4 ml) with stirring and cooling. The suspension formed was stirred for half an hour and filtered. The precipitate was washed with ether and placed in an exsiccator. The melting point of the crude product was 120°–122°C.

B. Pivaloyloxymethyl 6-[(hexahydro-1H-azepin-1-yl)-methyleneamino]-penicillanate To an ice-cold solution of pivaloyloxymethyl 6-aminopenicillanate (3.3 g) and N,N-diisopropylethylamine (1.7 ml) in pure chloroform (35 ml) was added the above prepared iodide (2.9 g). After 20 hours at 0°–5°C, the solution was evaporated in vacuo, and the residue was crystallized from acetone-water yielding a product with a melting point of 119°–120°C. The IR spectrum was identical with that of an authentic sample.

EXAMPLES 16 to 47

Following the procedures of the foregoing Examples, the compounds of Table I according to formula V were obtained.

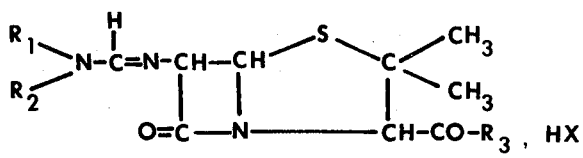

V

Table I

| Ex. No. | $R_1$ | $R_2$ | $R_3$ | HX |
|---|---|---|---|---|
| 16 | ethyl | ethyl | pivaloyloxymethoxy | $HNO_3$ |
| 17 | propyl | propyl | — | $HNO_3$ |
| 18 | ethyl | isopropyl | — | $HNO_3$ |
| 19 | isopropyl | isopropyl | — | $HNO_3$ |
| 20 | allyl | allyl | — | HCl |
| 21 | methyl | n-butyl | — | $HNO_3$ |
| 22 | ethyl | tert.butyl | — | HCl |
| 23 | methyl | cyclopentyl | — | |
| 24 | methyl | cyclohexyl | — | |
| 25 | ethyl | cyclohexyl | | |
| 26 | methyl | cycloheptyl | — | |
| 27 | methyl | cyclohexylmethyl | — | |
| 28 | methyl | benzyl | — | |
| 29 | methyl | p-chlorobenzyl | — | $HNO_3$ |
| 29a | methyl | m-bromobenzyl | — | |
| 29b | methyl | o-chlorobenzyl | — | |
| 30 | ethyl | 2-chloroethyl | — | HCl |
| 31 | methyl | phenyl | — | |
| 32 | methyl | bornyl | — | HCl |
| 33 | n-heptyl | n-heptyl | — | $(COOH)_2$ |

Table I-continued

| Ex. No. | R₁ | R₂ | R₃ | HX |
|---|---|---|---|---|
| 34 | methyl | methyl | benzoyloxymethoxy | HCl |
| 35 | methyl | methyl | phenacyloxy | (COOH)₂ |

| Ex. No. | R₁R₂N | | R₃ | HX |
|---|---|---|---|---|
| 36 | pyrrolidyl-1 | | pivaloyloxymethoxy | HNO₃ |
| 37 | piperidyl-1 | | — | |
| 38 | 2-methyl-piperidyl-1 | | — | HNO₃ |
| 39 | 3-methyl-piperidyl-1 | | — | |
| 40 | 4-methyl-piperidyl-1 | | — | |
| 41 | 2,6-dimethyl-piperidyl-1 | | — | |
| 42 | hexahydro-1H-azepin-1-yl | | benzyloxy | HCl |
| 43 | — | | cyanomethoxy | HCl |
| 44 | hexahydro-1(2H)-azocinnyl | | pivaloyloxymethoxy | |
| 45 | 1,2,3,4-tetrahydro-iso-quinolyl-2 | | — | |
| 46 | 4-methyl-piperazinyl-1 | | — | (HNO₃)₂ |
| 47 | morpholinyl-4 | | — | HNO₃ |

In the Table II below are listed the physical constants of the compounds of Table I, and the reaction conditions are shown:

Table II

| | Amide halide preparation | | | | | Rotation $[\alpha]_D^{20}$ in ethanol (96%) |
|---|---|---|---|---|---|---|
| Ex. No. | Halogenating agent | Solvent | Reaction time in h. | Recrystallized from | M.P. °C | |
| 16 | (COCl)₂ | Ether | 1 | Acetone-ether | 145–145.5 | +202 |
| 17 | (COCl)₂ | Ether | 2 | Acetone-ether | 121–122 | +196 |
| 18 | (COCl)₂ | Ether | 1 | Acetone-ether | 140.5 | +198 |
| 19 | (COCl)₂ | Ether | 2 | Methanol-ether | 158.3–158.4 | +177 |
| 20 | COCl₂ | Toluene | 2 | Ethanol-ether | 131–131.5 | +205 |
| 21 | (COCl)₂ | Ether | 2 | Ethylacetate-ether | 124–125 | +188 |
| 22 | (COCl)₂ | Ether | 16 | Isopropanol-ether | 163.5–164.5 | +195 |
| 23 | (COCl)₂ | Ether | 20 | Cyclohexane | 87–88 | +219 |
| 24 | (COCl)₂ | Ether | 5 | Ethanol-water | 73.5–74 | +202 |
| 25 | (COCl)₂ | Ether | 17 | Ethanol-water | 73.5–74 | +211 |
| 26 | (COCl)₂ | Ether | 3–4 | Petrol-ether | 97–99 | +201 |
| 27 | (COCl)₂ | Ether | 3.5 | Ethanol-water | 75–76 | +216 |
| 28 | (COCl)₂ | Ether | 2 | Acetone-water | 102–104 | +213 |
| 29 | (COCl)₂ | Ether | 16 | Methanol-ether | 163.5 | +183 |
| 30 | (COCl)₂ | Ether | 2 | Ethanol-ether | 120 | +183 |
| 31 | COCl₂ | Toluene | 19 | Acetone-water | 87.5–88.5 | +119 |
| 32 | (COCl)₂ | Ether | 0.5 | Methanol-ether | 191–191.5 | +161 |
| 33 | (COCl)₂ | Ether | 0.5 | Acetone-water | 80–84 | +155 |
| 34 | (COCl)₂ | Ether | 0.5 | Ethanol-ether | 158–160 | +209 |
| 35 | (COCl)₂ | Ether | 0.33 | Ethanol-ether | 127–128 | +201 |
| 36 | (COCl)₂ | Ether | 17.5 | Ethanol-ether | 116.5–117 | +182 |
| 37 | (COCl)₂ | Ether | 20 | Isopropanol-water | 102–103 | +206 |
| 38 | (COCl)₂ | Ether | 20 | Acetone-ether | 156.5–157 | +172 |
| 39 | (COCl)₂ | Ether | 20 | Petrol-ether | 70–71 | +209 |
| 40 | (COCl)₂ | Ether | 20 | Acetone-water | 96.5–97.5 | +218 |
| 41 | (COCl)₂ | Ether | 20 | Acetone-water | 91–93 | +205 |
| 42 | (COCl)₂ | Ether | 3.5 | Ethanol-acetone-ether | 177.5–178 | +226 |
| 43 | (COCl)₂ | Ether | 3.5 | Acetonitrile-ether | 163.5–164 | +237 |
| 44 | (COCl)₂ | Ether | 16 | Cyclohex- | 125.5 | +222 |

Table II.-continued

| Amide halide preparation | | | | | Rotation |
|---|---|---|---|---|---|
| Ex. No. | Halogenating agent | Solvent | Reaction time in h. | Recrystallized from | M.P. °C | $[\alpha]_D^{20}$ in ethanol (96%) |
| 45 | $(COCl)_2$ | Ether | 16.5 | Cyclohexane | 112–113 | +210 |
| 46 | $COCl_2$ | Toluene | 2 | Methanol-ether | 156.5–157 | +136 |
| 47 | $(COCl)_2$ | Ether | 19 | Methanol-ether | 148.5 | +167 |

EXAMPLE 48

6-[(Hexahydro-1H-azepin-1-yl)-methyleneamino]-penicillanic acid dihydrate

A. 1-Hexamethyleneiminecarboxaldehyde dimethyl acetal was prepared from the N-formylhexamethyleneimine-dimethyl sulfate complex by reaction with sodium methoxide according to the method of Bredereck et al. (Chem.Ber. 101, 41 (1968)). The boiling point was 83°–84°C/12 mm Hg.

B. 6-[(Hexahydro-1H-azepin-1-yl)-methyleneamino]-penicillanic acid dihydrate

A solution of the above mentioned acid amide acetal (4.1 g) in dry ether (100 ml) was slowly added to a solution of trimethylsilyl 6-aminopenicillanate (6.8 g) in ether (500 ml) at −30°C with stirring. The temperature was raised to 0°C within half an hour. Water (300 ml) was added. The stirring was continued for ten minutes after which the aqueous phase was separated, extracted with ether and freeze-dried. The solid product was crystallized from methanol-acetone. It melted with decomposition from 135° to 142°C.

EXAMPLE 49

6-[(Hexahydro-1H-azepin-1-yl)-methyleneamine]-penicillanic acid 16.7 g of benzyl 6-[(hexahydro-1H-azepin-1-yl)-methyleneamino]-penicillanate hydrochloride were suspended in ethyl acetate (550 ml) under continuous stirring and cooling in an ice bath. A solution of sodium bicarbonate (14.3 g) in water (400 ml) was added. The organic phase was separated and extracted with water (350 ml). After drying, the organic phase was evaporated in vacuo.

The oily residue was dissolved in methanol (150 ml) and hydrogenated with palladium on charcoal catalyst (10%, 11.4 g) at room temperature and under one atmosphere of hydrogen until the absorption of hydrogen ceased (about 15 minutes). The catalyst was filtered off and washed with methanol. The filtrate was evaporated in vacuo. The oily residue was crystallized from methanol (15 ml) - acetone (190 ml). The precipitate was filtered off, washed with acetone (2 × 10 ml) and dried in a vacuum exsiccator. The melting point was 156°C (dec.). $[\alpha]_D^{20}$ : +285° (c=1, 0.1 N HCl).

EXAMPLE 50

Acetoxymethyl 6-(N,N-dimethylformamidino-N′)-penicillanate hydrochloride

Acetoxymethyl 6-aminopenicillanate was liberated from 5.1 g of the p-toluenesulfonate according to the procedure of Example 1 and dissolved in dry chloroform (30 ml). Dry triethylamine (2.8 ml) was added, and the solution as cooled to −40°C. A solution of chlorodimethylformiminium chloride (1.3 g) in dry chloroform (15 ml) was slowly added with stirring a −20°C. In the course of three-fourth hour the temperature was allowed to raise to 0°C. The solution was evaporated in vacuo, and the residue was triturated with ether (200 ml). After filtration, 1.0 ml of a solution of dry hydrogen chloride in isopropanol (8 N) was added at 0°C with stirring. An amorphous product was obtained.

| NMR spectrum (10% w/v $CDCl_3$): | | | |
|---|---|---|---|
| $C_{(2)}(CH_3)_2$ | 3 H | s | at 1.54 |
|  | 3 H | s | at 1.74 |
| $OCOCH_3$ | 3 H | s | at 2.13 |
| $N(CH_3)_2$ | 6 H | broad s | at 3.43 |
| $C_{(3)}H$ | 1 H | s | at 4.58 |
| $C_{(5)}H+C_{(6)}H$ | 2 H | s | at 5.65 |
| $OCH_2O$ | 2 H | ABq | d 5.76 (J=5.5) / d 5.86 (J=5.5) |
| N—CH=N | 1 H | broad line | at 8.13 |

In this and the following Examples, the chemical shifts are given as ppm in ε values with TMS (0 ppm) an internal standard. Coupling constants (J) are in cps.

EXAMPLE 51

Pivaloyloxymethyl 6-(N-ethyl-N-β-ethoxyethylformamidino-N′)-penicillanate

A. N-Ethyl-N-β-ethoxyethylformamide
was prepared from the amine by reaction with chloral. The boiling point was 102°–104°C/11 mm Hg.

B. Chloro-(ethyl-β-ethoxyethyl)-formiminium chloride
3.4 ml of oxalyl chloride dissolved in dry ether (20 ml) were slowly added to a solution of N-ethyl-N-β-ethoxyethylformamide (5.8 g) in dry ether (60 ml) at 0°C with stirring. After stirring at room temperature for one hour, the ether was decanted from the oily amide chloride which was triturated twice with ether and stored in an exsiccator.

C. Pivaloyloxymethyl 6-(N-ethyl-N-β-ethoxyethylformamidino-N′)-penicillanate 5 g of the crude amide chloride were dissolved in dry chloroform (30 ml) and added dropwise to a solution of pivaloyloxymethyl 6-aminopenicillanate (6.6 g) and triethylamine (7 ml) in dry chloroform (30 ml) at −30°C to −40°C with stirring. The temperature was raised to 0°C within three-fourth hour. The solution was evaporated in vacuo, and the residue was treated with ether (400 ml). Afte filtration from triethylamine hydrochloride, the filtrate was evaporated in vacuo. The oily residue was dissolved in 350 ml of diluted hydrochloric acid at a pH of about 3. After filtration with Dicalite filter aid (diatomaceous earth), the filtrate was made alkaline with sodium bicarbonate to a pH of about 7.5 and extracted with ether. After drying, the ether was removed in vacuo leaving an oil which could not be crystallized.

NMR spectrum (10% w/v CDCl₃):

| | | |
|---|---|---|
| N—CH₂—CH₃ | 3 H t | at 1.13 (J=6.5) |
| OCH₂CH₃ | 3 H t | at 1.17 (J=6.5) |
| C(CH₃)₃ | 9 H s | at 1.20 |
| C₍₂₎(CH₃)₂ | 3 H s | at 1.49 |
| | 3 H s | at 1.65 |
| —CH₂—N—CH₂— ⎫ ⁺⁾<br>OCH₂           ⎭ | 6 H m | at 3.1 – 3.7 |
| C₍₃₎H | 1 H s | at 4.38 |
| C₍₆₎H | 1 H dd | at 5.04 (J=4.0, J=1) |
| C₍₅₎H | 1 H d | at 5.47 (J=4.0) |
| OCH₂O | 2 H ABq | { 5.75 (J=5.0)<br>  5.88 (J=5.5) } |
| N—C=N | 1 H d | at 7.60 (J=1) |

⁺⁾ overlapping bands

EXAMPLE 52

Pivaloyloxymethyl 6-(N-butyl-N-β-cyanoethylformamidino-N')-penicillanate

A. N-Butyl-β-formamidoprpionitrile
was prepared -formamidopropionitrile formylation of β-N-butylaminopropionitrile with chloral. The boiling point was 114°–115°C/0.4 mm Hg.

B. Chloro-(butyl-β-cyanoethyl)-formiminimum chloride 1.7 ml of oxalyl chloride dissolved in dry ether (10 ml) were slowly added to a solution of N-butyl-β-formamidopropionitrile (3.1 g) in dry ether (30 ml) a 0°C with stirring. After stirring at room temperature for two hours, the ether was decanted from the oily amide chloride. The crude amide chloride was treated twice with fresh ether and kept in an exsiccator.

C. Pivaloyloxymethyl 6-(N-butyl-N-β-cyanoethylformamidino-N')-penicillanate

A solution of the crude amide chloride (2.3 g) in dry chloroform (15 ml) was added dropwise to a solution of pivaloyloxymethyl 6-aminopenicillanate (3.3 g) and triethylamine (3.1 ml) in dry chloroform at −20°C to −30°C with stirring. The temperature was kept at −20°C for half an hour and then raised to 0°C in the course of a quarter of an hour. The solvent was removed in vacuo, and the residue was triturated with ether (200 ml). After filtration from triethylammonium chloride, the filtrate was concentrated to a volume of 50 ml in vacuo and extracted with 75 ml of diluted hydrochloric acid (pH about 3). The aqueous phase was filtered with Dicalite and made alkaline to a pH of about 7.5. The oily product was extracted with ether. The ethereal phase was dried and evaporated in vacuo leaving an oil which did not crystallize.

NMR spectrum (10% w/v CDCl₃):

| | | |
|---|---|---|
| CH₃CH₂CH₂CH₂N | 3 H t | at 0.95 (J=6) |
| C(CH₃)₃ | 9 H s | at 1.23 |
| C₍₂₎(CH₃)₂ | 3 H s | at 1.51 |
| | 3 H s | at 1.65 |
| CH₃CH₂CH₂CH₂N | 4 H m | at 1.20–1.60 |
| CH₂CN | 2 H t | at 2.79 (J=6.5) |
| CH₂HCH₂ | 4 H m | at 3.10–3.70 |
| C₍₃₎H | 1 H s | at 4.41 |
| C₍₆₎H | 1 H dd | at 5.03 (J=4, J=1) |
| C₍₅₎H | 1 H d | at 5.50 (J=4) |
| OCH₂O | 2 H ABq | { d 5.77 (J=6.0)<br>  5.90 (J=6.0) } |

-continued

| | | |
|---|---|---|
| N—CH=N | 1 H d | at 7.62 (J=1) |

EXAMPLE 53

Pivaloyloxymethyl 6-(N-methyl-N-carbomethoxymethylformamidino-N')-penicillanate

A. Chloro-(methyl-carbomethoxymethyl)-formiminium chloride 3.0 g of phosgene in dry benzene (16 ml) were slowly added to a solution of methyl N-formyl-N-methylglycinate (2.0 g) in dry benzene (15 ml) a 0°C with stirring. The reaction mixture was stirred overnight at room temperature and evaporated in vacuo. The oily residue was triturated twice with ether and kept in an exsiccator.

B. Pivaloyloxymethyl 6-(N-methyl-N-carbomethoxymethylformamidino-N')-penicillanate A solution of the crude amide chloride (2.4 g) in dry chloroform (15 ml) was slowly added to a solution of pivaloyloxymethyl 6-aminopenicillanate (3.3 g) and triethylamine (3.4 ml) in dry chloroform (15 ml) at −20°C to −30°C with stirring. The temperature was raised to 0°C during three-fourth hour, and the solvent was removed in vacuo. The residue was treated with ether (200 ml). The precipitate was filtered off, and the filtrate was concentrated to a volume of 50 ml in vacuo. This solution was extracted with diluted hydrochloric acid (75 ml, pH about 3), and the aqueous phase was filtered with Dicalite. By addition of sodium bicarbonate to a pH of about 7.5, an oil was formed which was taken up in ether. The ethereal phase was dried and evaporated to leave an oil which did not crystallize.

NMR spectrum (10% w/v CDCl₃):

| | | |
|---|---|---|
| C(CH₃)₃ | 9 H s | at 1.23 |
| C₍₂₎(CH₃)₂ | 3 H s | at 1.50 |
| | 3 H s | at 1.65 |
| N—CH₃ | 3 H s | at 2.97 |
| OCH₃ | 3 H s | at 3.73 |
| NCH₂CO | 2 H ABq | at 4.00 |
| C₍₃₎H | 1 H s | at 4.38 |
| C₍₆₎H | 1 H dd | at 5.08 (J=4.4, J=1) |
| C₍₅₎H | 1 H d | at 5.47 (J=4.4) |
| OCH₂O | 2 H ABq | { d 5.77 (J-5.5)<br>  d 5.89 (J=5.5) } |
| N—CH=N | 1 H d | at 7.67 (J=1) |

EXAMPLE 54

Pivaloyloxymethyl 6-(N-methyl-N-carbamylmethylformamidino-N')-penicillanate

To an ice-cold solution of pivaloyloxymethyl 6-aminopenicillanate (6.6 g) and triethylamine (5.6 ml) in dry chloroform (70 ml) was added 1.1-dichlorodimethyl ether (2.3 g) with stirring. The solution was kept overnight at room temperature and then cooled to 0°C. Sarcosinamide (1.8 g) was added. The reaction mixture was kept for 48 hours at 0°C, after which the solvent was removed in vacuo. The residue was distributed between ether (75 ml) and diluted hydrochloric acid (75 ml, pH about 3). The aqueous phase was separated and extracted with ether (25 ml) and then made alkaline (to a pH of about 7.5) with sodium bicarbonate. The oily product was taken up in ether, which was dried and evaporated in vacuo. The residue did not cyrstallize

| NMR spectrum (10% w/v CDCl$_3$): | | | |
|---|---|---|---|
| C(CH$_3$)$_3$ | 9 H | s | at 1.22 |
| C$_{(2)}$(CH$_3$)$_2$ | 3 H | s | at 1.51 |
| | 3 H | s | at 1.65 |
| NCH$_3$ | 3 H | s | at 2.99 |
| NCH$_2$CO | 2 H | s | at 3.92 |
| C$_{(3)}$H | 1 H | s | at 4.43 |
| C$_{(6)}$H | 1 H | dd | at 5.05 (J=4.1, J=1) |
| C$_{(5)}$H | 1 H | d | at 5.52 (J-4.1) |
| OCH$_2$O | 1 H | ABq | { 5.88 (J=5.5) |
| | | | 5.78 (J=5.5) } |
| N—CH=N | 1 H | d | at 7.66 (J=1) |

EXAMPLE 55.

Pivaloyloxymethyl 6-(N-ethyl-N-β-hydroxyethylformamidino-N')-penicillanate

Pivaloyloxymethyl 6-aminopenicillanate (6.6 g) was treated with 1.1-dichlorodimethyl ether and triethylamine as in Example 54. To the ice-cold solution was added 2-ethylaminoethanol (1.8 g). After 48 hours at 0°C, the solution was evaporated in vacuo, and the residue was triturated with acetone (25 ml). Triethylamine hydrochloride was filtered off, and the filtrate was evaporated in vacuo. The residue was distributed between ether (75 ml) and diluted hydrochloric acid (75 ml, pH about 2.5). The aqueous phase was separated and made alkaline to a pH of about 7.5. The oily reaction product was taken up in ether. Drying and evaporation in vacuo gave an oil which did not crystallize.

| NMR spectrum (10% w/v CDCl$_3$): | | | |
|---|---|---|---|
| CH$_3$CH$_2$N | 3 H | t | at 1.1 (J=7) |
| C(CH$_3$)$_3$ | 9 H | s | at 1.22 |
| C$_{(2)}$(CH$_3$)$_2$ | 3 H | s | at 1.49 |
| | 3 H | s | at 1.65 |
| *)CH$_3$CH$_2$N | 2 H | q | at 3.28 (J=7) |
| *)N—CH$_2$—CH$_2$OH | 2 H | m | at 3.5 |
| *)N—CH$_2$—CH$_2$OH | 2 H | m | at 3.7 |
| C$_{(3)}$H | 1 H | s | at 4.43 |
| C$_{(6)}$H | 1 H | dd | at 4.98 (J=4.1, J about 0.8) |
| C$_{(5)}$H | 1 H | d | at 5.49 (J=4.1) |
| OCH$_2$O | 1 H | ABq | d 5.77 (J=5.5) |
| | 1 H | | d 5.88 (J=5.5) |
| N—CH=N | 1 H | d | at 7.67 (J about 0.8) |

*)partly overlapped by other bands

EXAMPLE 56

Pivaloyloxymethyl 6-(N-methyl-N-carbethoxymethylformamidino-N')-penicillanate

Pivaloyloxymethyl 6-aminopenicillanate (6.6 g) was treated with 1.1-dichlorodimethyl ether and triethylamine as described in Example 54. Ethyl N-methylglycinate (2.3 g) was added to the ice-cold solution. The reaction mixture was kept in an ice-box for 48 hours and then worked up as in Example 55. The product was an oil which did not crystallize.

| NMR spectrum (10% w/v CDCl$_3$): | | | |
|---|---|---|---|
| C(CH$_3$)$_3$ | 9 H | s | at 1.22 |
| OCH$_2$CH$_3$ | 3 H | t | at 1.28 |
| C$_{(2)}$(CH$_3$)$_2$ | 3 H | s | at 1.51 |
| | 3 H | s | at 1.66 |
| NCH$_3$ | 3 H | s | at 2.98 |
| NCH$_2$CO | 2 H | ABq | at 4.01 |
| OCH$_2$CH$_3$ | 2 H | q | at 4.23 (J=7) |
| C$_{(3)}$H | 1 H | s | at 4.39 |

-continued

| | | | |
|---|---|---|---|
| C$_{(6)}$H | 1 H | dd | at 5.12 (J=4.2, J=1) |
| C$_{(5)}$H | 1 H | d | at 5.48 (J=4.2) |
| OCH$_2$O | (1 H | ABq | { d 5.78 (J=5.8) |
| | (1 H | | { d 5.87 (J=5.8) } |
| N—CH=N | 1 H | d | at 7.69 (J=1) |

EXAMPLE 57

Pivaloyloxymethyl 6-(N-methyl-N-furfurylformamidino-N')-penicillanate

By following the procedure of Example 55 and substituting 2-ethylaminoethanol with N-methylfurfurylamine (2.3 ml) an oil was obtained which did not crystallize

| NMR spectrum (10% w/v CDCl$_3$): | | | |
|---|---|---|---|
| C(CH$_3$)$_3$ | 9 H | s | at 1.22 |
| C$_{(2)}$(CH$_3$)$_2$ | 3 H | s | at 1.51 |
| | 3 H | s | at 1.66 |
| NCH$_3$ | 3 H | s | at 2.84 |
| (furan)—CH$_2$—N | 2 H | bs | at 4.35 |
| C$_{(3)}$H | 1 H | s | at 4.40 |
| C$_{(6)}$H | 1 H | dd | at 5.10 (J=4.5, J=1) |
| C$_{(5)}$H | 1 H | d | at 5.48 (J=4.5) |
| OCH$_2$O | (1 H | ABq | d 5.77 (J=5) |
| | (1 H | | d 5.81 (J=5) |
| (furan H,H) | 2 H | m | at 6.2–6.4 |
| (furan H) | 1 H | m | at 7.3–7.4 |
| N—CH=N | 1 H | d | at 7.69 (J=1) |

By following the procedure of Example 55, and substituting 2-ethylaminoethanol with N-methyl-2-thenylamine, N-n-butyl-β-2-thiopheneethylamine, 3-(ethylaminomethyl)-pyridine, and 4-(methylaminomethyl)-pyridine, the pivaloyloxymethyl 6-(N-methyl-N-2-thenylformamidino-N')-penicillanate, the pivaloyloxymethyl 6-(N-n-butyl-N-β-2-thiopheneethylformamidino-N')-penicillanate, the pivaloyloxymethyl 6-(N-ethyl-N-3-pyridylmethylformamidino-N-')-penicillanate and the pivaloyloxymethyl 6-(N-methyl-N-4-pyridylmethylformamidino-N')-penicillanate can be obtained.

EXAMPLE 58

Pivaloyloxymethyl 6-[4'-dimethylcarbamylpiperazinyl-1')-methyleneamino]-penicillanate By following the procedure of Example 55 and substituting 2-ethylaminoethanol with 1-dimethylcarbamylpiperazine (3.1 g), an amorphous solid was obtained which could not be crystallized.

| NMR spectrum (10% w/v CDCl$_3$): | | | |
|---|---|---|---|
| C(CH$_3$)$_3$ | 9 H | s | at 1.22 |
| C$_{(2)}$(CH$_3$)$_2$ | 3 H | s | at 1.51 |
| | 3 H | s | at 1.66 |
| N(CH$_3$)$_2$ | 6 H | s | at 2.85 |
| NCH$_2$ | 8 H | m | at 3.0–3.6 |

-continued

| | | | |
|---|---|---|---|
| $C_{(3)}H$ | 1 H | s | at 4.38 |
| $C_{(6)}H$ | 1 H | dd | at 5.07 (J=4.5, J=1) |
| $C_{(5)}H$ | 1 H | d | at 5.48 (J=4.5) |
| $OCH_2O$ | 1 H ABq | d | 5.77 (J=6) |
| | 1 H | d | 5.90 (J=6) |
| N—CH=N | 1 H | d | at 7.63 (J=1) |

EXAMPLE 59

Acetoxymethyl 6-[(hexahydro-1H-azepin-1-yl)-methyleneamino]-penicillanate hydrochloride A solution of the crude amide chloride (16.9 g), prepared from N-formylhexamethyleneimine as described in Example 1, in dry chloroform (135 ml) was slowly added to a solution of acetoxymethyl 6-aminopenicillanate p-toluenesulfonate (43 g) and triethylamine (39.4 ml) in chloroform (275 ml) at −50°C with stirring. The temperature was raised to 0°C during one hour. The solvent was removed in vacuo, and the oily residue was triturated with acetone (250 ml). A precipitate formed and was filtered off, and the filtrate was evaporated in vacuo. The residue was dissolved in ether (350 ml) and extracted with diluted hydrochloric acid at a pH of about 3 (350 ml). The aqueous phase was made alkaline (to pH about 7.5) and extracted with ether (500 ml). After drying, the ether was removed in vacuo, and the oily residue was dissolved in tert.butanol (230 ml) and treated with 8.85 ml of a solution of dry hydrogen chloride in isopropanol (8 N) a 0° C with stirring. Ether (150 ml) was added. The precipitate was filtered off and recrystallized from a mixture of acetone (400 ml) and ether (250 ml) to yield the analytically pure product with a melting point of 141.5°–142.5°C. $[\alpha]_D^{20}$ : + 226° (c=1, 96% $C_2H_5OH$).

EXAMPLE 60

Pivaloyloxymethyl 6-[(octahydro-1H-azonin-1-yl)-methyleneamino]-penicillanate.

A. N-Formyloctamethyleneimine was prepared from octamethyleneimine and chloral. The boiling point was 141°–143°C/10 mm Hg.

B. Pivaloyloxymethyl 6-[(octahydro-1H-azonin-1-yl)-methyleneamino]-penicillanate 1.7 g of N-formyloctamethyleneimine was dissolved in 50 ml of dry ether. While stirring and cooling, 0.94 ml of oxalyl chloride in 5 ml of dry ether was added dropwise. The mixture was stirred for 3 ½ hours at room temperature. The precipitated amide chloride was filtered off and washed with dry ether. It was kept in an exsiccator.

The crude amide chloride (1.3 g) was dissolved in chloroform (15 ml) and slowly added to a solution of triethylamine (1.75 ml) and pivaloyloxymethyl 6-aminopenicillanate (1.65 g) in dry chloroform (15 ml) at −40°C with stirring. The temperature was raised to 0°C during 45 minutes. The solution was evaporated in vacuo, and the residue was triturated with acetone (25 ml). After filtration, the filtrate was evaporated in vacuo. The residue was taken up in ether (50 ml) and extracted with diluted hydrochloric acid (50 ml) at a pH of about 3. The aqueous phase was made alkaline (pH about 7.5). The precipitate was recrystallized from a mixture of acetone (15 ml) and water (10 ml) to yield the analytically pure product with a melting point of 106°–107°C. $[\alpha]_D^{20}$ : (c=1, 96% $C_2H_5OH$).

EXAMPLE 61

Pivaloyloxymethyl 6-(N-ethyl-N-phenethylformamidino-N′)-penicillanate

A. N-Ethyl-N-phenethylformamide was prepared from N-ethylphenethylamine and chloral. The boiling point was 107°–108°C/0.4 mm Hg.

B. Pivaloyloxymethyl 6-(N-ethyl-N-phenethylformamidino-N′)-penicillanate

To a solution of N-ethyl-N-phenethylfomamide (3.6 g) in dry ether (100 ml) at 0°C was slowly added oxalyl chloride (1.7 ml) in dry ether (10 ml) with stirring. The mixture was stirred overnight at room temperature. The crude amide chloride was filtered off and washed with ether. It was kept in an exsiccator.

A solution of the amide chloride (2.6 g) in dry chloroform (15 ml) was added dropwise to a solution of triethylamine (3.1 ml) and pivaloyloxymethyl 6-aminopenicillanate (3.3 g) in chloroform (15 ml) at −20°C with stirring. The temperature was raised to 0°C during 45 minutes. The solution was evaporated in vacuo, and the residue was triturated with ether (200 ml). After filtration, the filtrate was evaporated in vacuo, and the oily residue was dissolved in diluted hydrochloric acid (300 ml) at a pH of about 3 and filtered with Dicalite. The filtrate was made alkaline (pH about 7.5) and extracted with ether (200 ml). The etheral phase was dried and evaporated in vacuo to leave an oil which did not crystallize.

| NMR spectrum (10% w/v $CDCl_3$): | | | |
|---|---|---|---|
| $N-CH_2-CH_3$ | 3 H | s | at 1.10 (J=7) |
| $C(CH_3)_3$ | 9 H | s | at 1.22 |
| $C_{(2)}(CH_3)_2$ | 3 H | s | at 1.50 |
| | 3 H | s | at 1.66 |
| $N-CH_2-CH_2-$⌬ | 2 H | m | at 2.83 |
| | 2 H | m | at 3.43 |
| $N-CH_2-CH_3$ | 2 H | q | at 3.18 (J=7) |
| $C_{(3)}H$ | 1 H | s | at 4.42 |
| $C_{(6)}H$ | 1 H | dd | at 5.03 (J=1, J=4) |
| $C_{(5)}H$ | 1 H | d | at 5.51 (J=4) |
| $OCH_2$ ABq | 1 H | d | at 5.78 (J=5.5) |
| | 1 H | d | at 5.91 (J=5.5) |
| ⌬ | 5 H | s | at 7.27 |
| N—CH=N | 1 H | d | at 7.58 (J=1) |

EXAMPLE 62

Pivaloyloxymethyl 6-(N-ethyl-N-β-phenoxyethylformamidino-N′)-penicillanate

A. N-Ethyl-N-β-phenoxyethylformamide

To a solution of formic acid (3.3 ml) and N-ethyl-N-β-phenoxyethylamine (14.5 g) in methylene chloride (100 ml) at 0°–5°C was added N,N′-dicyclohexylcarbodiimide (19.7 g) with stirring. The mixture was stirred for 18 hours at room temperature and filtered. The filtrate was evaporated in vacuo to leave an oil which was taken up in either (100 ml) and extracted with 0.4 N hydrochloric acid (2 × 25 ml) and water (2 × 25 ml). After drying, the ether was removed in vacuo to leave the above compound as an oil.

B. Chloro-(ethyl-β-phenoxyethyl)-formiminium chloride 1.7 ml of oxalyl chloride dissolved in dry ether (5 ml) was slowly added to a solution of the crude N-ethyl-N-β-phenoxyethylformamide (3.9 g) in dry ether (25 ml) at 0°C with stirring. After stirring for 3 hours at room temperature, the ether was decanted from the oily amide chloride which was twice triturated with ether and stored in an exsiccator.

C. Pivaloyloxymethyl 6-(N-ethyl-N-β-phenoxyethylformamidino-N')-penicillanate 2.8 g of the crude amide chloride were dissolved in dry chloroform (30 ml) and added dropwise to a solution of pivaloyloxymethyl 6-aminopenicillanate (3.3 g) and triethylamine (3.5 ml) in dry chloroform (30 ml) at −40°C with stirring. The temperature was gradually raised to 0°C within 45 minutes. The solution was evaporated in vacuo, and the residue was triturated with ether (200 ml). After filtration from triethylamine hydrochloride, the filtrate was extracted with diluted hydrochloric acid (100 ml) at a pH of about 3. The aqueous phase was separated, filtered with Dicalite filter aid, made alkaline with sodium bicarbonate to a pH of about 7.5, and extracted with ether. After drying, the ether was removed in vacuo to leave an oil which could not be crystallized.

| NMR spectrum (10% w/v CDCl$_3$): | | |
|---|---|---|
| CH$_3$CH$_2$ | 3 H m | at 1.20 |
| C(CH$_3$)$_3$ | 9 H s | at 1.23 |
| C$_{(2)}$(CH$_3$)$_2$ | 3 H s | at 1.50 |
|  | 3 H s | at 1.65 |
| N—CH$_2$—CH$_3$ | 2 H m | at 3.37 |
| N—CH$_2$—CH$_2$O | 2 H t | at 3.62 (J=5.5) |
| N—CH$_2$—CH$_2$O | 2 H t | at 4.17 (J=5.5) |
| C$_{(3)}$H | 1 H s | at 4.40 |
| C$_{(6)}$H | 1 H dd | at 5.07 (J=4, J=1) |
| C$_{(5)}$H | 1 H d | at 5.50 (J=4) |
| OCH$_2$O | 2 H ABq | (d 5.78 (J=5) |
|  |  | (d 5.89 (J=5) |
| C$_6$H$_5$O | 5 H m | at 6.7–7.5 |
| N—CH=N | 1 H d | at 7.68 (J=1) |

EXAMPLE 63

Pivaloyloxymethyl 6-(N-methyl-N-cabobenzyloxymethylformamidino-N')-penicillanate To a solution of pivaloyloxymethyl 6-aminopenicillanate (9.9 g) in dry ether (150 ml) was added propyl formimidate hydrochloride (4.1 g) at room temperature. The mixture was stirred for 40 minutes. Benzyl sarcosinate (5.6 g) was added, and the reaction mixture was kept in the refrigerator for 18 hours and finally stirred for 2 hours at room temperature. After that the reaction mixture was extracted with 50 ml of water at a pH about 7, and with 50 ml water at a pH. of about 2.5. The acid aqueous phase was filtered with Dicalite filter aid, made alkaline with sodium bicarbonate (pH about 7.5), and extracted with ethyl acetate (150 ml), the extract being dried and evaporated in vacuo. The oily residue was taken up in ether (50 ml) and extracted with 50 ml of water (pH about 3). The aqueous phase was extracted with 2 × 50 ml of ethyl acetate, filtered with Dicalite filter aid, and made alkaline with sodium bicarbonate (pH about 7.5). Extraction with ethyl acetate, drying, and evaporation in vacuo yielded an oil which did not crystallize.

| NMR spectrum (10% w/v CDCl$_3$): | | |
|---|---|---|
| C(CH$_3$)$_3$ | 9 H s | at 1.23 |
| C$_{(2)}$(CH$_3$)$_2$ | 3 H s | at 1.49 |
|  | 3 H s | at 1.63 |
| NCH$_3$ | 3 H s | at 2.98 |
| N—CH$_2$—CO | 2 H ABq | at 4.03 |
| C$_{(3)}$H | 1 H s | at 4.37 |
| C$_{(6)}$H | 1 H dd | at 5.09 (J=4, J=1) |
| C$_6$H$_5$—CH$_2$O | 2 H s | at 5.20 |
| C$_{(5)}$H | 1 H d | at 5.47 (J=4) |
| OCH$_2$O | 2 H Abq | (d 5.78 (J=6.5) |
|  |  | (d 5.90 (J=6.5) |
| C$_6$H$_5$ | 5 H s | at 7.37 |
| N—CH=N | 1 H d | at 7.68 (J=1) |

EXAMPLE 64

Preparation of tablets containing pivaloyloxymethyl 6-[(hexahydro-1H-azepin-1-yl)-methyleneamino]-penicillanate hydrochloride.

| Ingredients: | g |
|---|---|
| Pivaloyloxymethyl 6-[(hexahydro-1H-azepin-1-yl)-methyleneamino]-penicillanate hydrochloride | 350 |
| Polyvinylpyrrolidone | 10 |
| Corn starch | 40 |
| Magnesium stearate | 4 |

The pivaloyloxymethyl ester is screened through a sieve with 1.0 mm mesh openings. The powder is then wetted with a solution of polyvinylpyrrolidone in 150 ml of a solvent composed of 1 part of ethanol (96%) and 19 parts of acetone. The moist mass is passed through a sieve with 1.0 mm mesh openings and then dried at 30°C on trays or other conveient drying equipment, for instance a "fluidized bed" drying cupboard.

When the solvent has evaporated, the granules are sifted through a sieve with 0.7 mm mesh openings, and are finally mixed with the corn starch and magnesium stearate.

The granulate is compressed into tablets of 0.40 g weight using punches and dies of 12 mm diameter to yield 1000 tablets each containing 0.35 g of the pivaloyloxymethyl ester.

EXAMPLE 65

A pharmaceutical preparation for injection

In a sterile vial is placed a single dose of 250 mg of sterilized 6-[(hexahydro-1H-azepin-1-yl)-methyleneamino]-penicillanic acid. For administration by injection the compound is dissolved in 5 ml of sterile water.

EXAMPLE 66

Capsules, each containing 0.150 g of pivaloyloxymethyl 6-[(hexahydro-1H-azepin-1-yl)-methyleneamino]-penicillanate hydrochloride (FL 1039) and 0.175 g of pivaloyloxymethyl α-aminobenzylpenicillinate hydrochloride (VD 923) are prepared according to the following procedure:

| Ingredients: | |
|---|---|
| FL 1039 | 150 g |
| VD 923 | 175 g |
| Polyvinyl pyrrolidone | 10 g |

-continued

| | |
|---|---|
| Magnesium stearate | 4 g |

FL 1039 and VD 923 are mixed and passed through a 20 US Standard mesh sieve. After having been mixed again, the resulting powder is moistened with a solution of polyvinyl pyrrolidone in isopropanol (150 ml). The moistened mixture is granulated by passing it through a 20 US Standard mesh sieve and is afterwards dried by 30°C. For the drying operation, a conventional drying oven with trays, or other suitable drying apparatus, for instance functioning according to the fluidized bed principles, may be applied.

After drying, the granulate is passed through a 25 US Standard mesh sieve and is finally mixed with the magnesium stearate.

The finished granulate is filled into hard gelatine capsules No. 0, each capsule containing 0.349 g granulate, the above ingredients thereby corresponding to 1000 capsules.

EXAMPLE 67

Tablets, each containing 0.150 g of pivaloyloxymethyl 6-[(hexahydro-1H-azepin-1-yl)-methyleneamino]-penicillanate hydrochloride (FL 1039) and 0.175 g of pivaloyloxymethyl α-aminobenzylpenicillinate hydrochloride (VD 923) are prepared according to the following procedure:

| | |
|---|---|
| Ingredients: | |
| FL 1039 | 150 g |
| VD 923 | 175 g |
| Polyvinyl pyrrolidone | 10 g |
| Cellulose, microcrystalline | 175 g |
| Starch | 75 g |
| Magnesium stearate | 4 g |

FL 1039 and VD 923 are mixed and passed through a 20 US Standard mesh sieve. After having been mixed again, the resulting powder is moistened with a solution of polyvinyl pyrrolidone in isopropanol (150 ml). The moistened mixture is granulated by passing it through a 20 US Standard mesh sieve and is afterwards dried by 30°C. For the drying operation, a conventional drying oven with trays or other suitable drying apparatus, for instance funtioning according to the fluidized bed principle, may be applied.

After drying, the granulate is passed through a 25 US Standard mesh sieve and is afterwards mixed with the microcrystalline cellulose, the starch and the magnesium stearate. The graulate is compressed into tablets, each containing about 0.600 g, by using punches with a diameter of 13.5 mm, the above ingredients thereby corresponding to 1000 tablets each containing 0.150 g of FL 1039 and 0.175 g of VD 923.

I claim:

1. Amidino-penicillanic acid derivatives of the formula I:

in which $R_1$ is selected from the group consisting of alkyl, chloroalkyl and hydroxyl-alkyl having from 1 to 7 carbon atoms, alkoxyalkyl having from 2 to 7 carbon atoms, carbalkoxyalkyl having from 3 to 4 carbon atoms, cyanoalkyl and carbamylalkyl having from 2 to 3 carbon atoms, and allyl; $R_2$ is selected from the group consisting of alkyl, chloroalkyl and hydroxy-alkyl having from 1 to 7 carbon atoms, alkoxyalkyl having from 2 to 4 carbon atoms, carbalkoxyalkyl having from 3 to 4 carbon atoms, cyanoalkyl, or carbamylalkyl having from 2 to 3 carbon atoms and allyl; phenyl; phenyl substituted, chlorophenyl substituted, bromo-phenyl substituted, phenoxy substituted and carbobenzyloxy substituted methyl and ethyl; cycloalkyl and cycloalkylmethyl having from 5 to 7 carbon atoms; methyl and ethyl substituted with furyl; and $R_1$ and $R_2$ form a straight or branched alkylene chain which together with the nitrogen atom form a saturated heterocyclic ring having from 4 to 8 carbon atoms; and $R_1$ and $R_2$ furthermore together with the nitrogen atom form a heterocyclic radical selected from the group consisting of morpholinyl-4, 4-methyl-piperazinyl-1, and 1, 2, 3, 4-tetrahydroisoquinolyl-2; and $R_3$ is hydroxyl, chloroalkoxy, cyanomethyloxy, or benzyloxy, the alkoxy part of which has 1 to 4 carbon atoms; and alkanoyloxymethoxy having 3 to 7 carbon atoms; and pharmaceutically acceptable salts thereof.

2. The compounds as claimed in claim 1, in which $R_1$ and $R_2$ represent a pentamethylene, hexamethylene or heptamethylene radical linked into a ring with the nitrogen atom, and $R_3$ is a hydroxyl group or an alkanoyloxymethoxy group having from 3 to 7 carbon atoms.

3. 6-[(Hexahydro-1H-azepin-1-yl)-methyleneamino]-penicillanic acid, the pharmaceutically acceptable hydrolyzable esters thereof, and the pharmaceutically acceptable salts of the acid and of the said esters.

4. 6-[(Hexahydro-1H-azepin-1-yl)-methyleneamino]-penicillanic acid, and the pivaloyloxymethyl ester thereof.

5. 6-[(Piperidyl-1)-methyleneamino]-penicillanic acid, and the pivaloyloxymethyl ester thereof.

6. 6-[(Hexahydro-1(2H)-azocinyl)-methyleneamino]-penicillanic acid, and the pivaloyloxymethyl ester thereof.

7. 6-(N-ethyl-N-isopropyl-formamidino-N')-penicillanic acid, and the pivaloyloxymethyl ester thereof.

8. 6-(N-methyl-N-cyclopentyl-formamidino-N')-penicillanic acid, and the pivaloyloxymethyl ester thereof.

9. 6-[(2-Methyl-piperidyl-1)-methyleneamino]-penicillanic acid and the pivaloyloxymethyl ester thereof.

10. 6-[(4-Methyl-piperidyl-1)-methyleneamino]-penicillanic acid and the pivaloyloxymethyl ester thereof.

11. [(2,6-Dimethyl-piperidyl-1)-methyleneamino]-penicillanic acid and the pivaloyloxymethyl ester thereof.

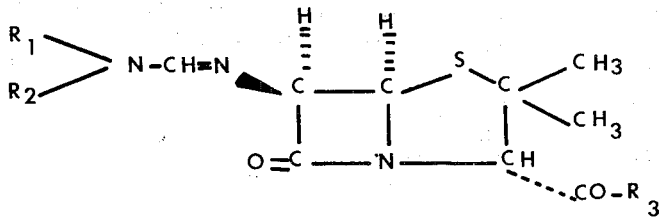

12. 6-[(Octahydro-1H-azocin-1-yl)-methyleneamino]-penicillanic acid and the pivaloyloxymethyl ester thereof.

13. 6-(N-methyl-N-cyclohexyl-formamidino-N')-penicillanic acid and the pivaloyloxymethyl ester thereof.

14. 6-(N,N-diethyl-formamidino-N')-penicillanic acid and the pivaloyloxymethyl ester thereof.

15. Amidino-penicillanic acid derivatives of formula I of claim 1, in which $R_1$ and $R_2$ form a straight or branched alkylene chain, which, together with the nitrogen atom represent a ring having from 4 to 8 carbon atoms, and $R_3$ is selected from the group consisting of hydroxyl and cyanomethyloxy, chloroalkoxy, benzyloxy, or an alkanoyloxymethoxy group, the alkyl of which has from 1 to 4 carbon atoms, and pharmaceutically acceptable salts thereof.

16. Amidino-penicillanic acid derivatives of the formula I of claim 1, in which $R_1$ and $R_2$ are selecged from the group consisting of alkyl, chloroalkyl and hydroxyalkyl having from 1 to 7 carbon atoms, alkoxyalkyl having up to 4 carbon atoms, carbalkoxyalkyl having from 3 to 4 carbon atoms, cyanoalkyl, cabamylalkyl having from 2 to 3 carbon atoms and allyl, and $R_3$ is selected from the group consisting of hydroxyl and cyanomethyloxy, chloroalkoxy, benzyloxy, or an alkanoyloxymethoxy group, the alkoxy of which has from 1 to 4 carbon atoms, and pharmaceutically acceptable salts thereof.

17. Amidino-penicillanic acid derivatives of formula I of claim 1, in which $R_1$ is methyl or ethyl and $R_2$ is a cycloalkyl or a cycloalkyl-methyl radical having from 5 to 7 carbon atoms in the ring, $R_3$ is selected from the group consisting of hydroxyl and cyaomethyloxy, chloroalkoxy, benzyloxy, or an alkanoyloxymethoxy group, the alkoxy of which has from 1 to 4 carbon atoms, and pharmaceutically acceptable salts thereof.

18. Amidino-penicillanic acid derivatives of formula I of claim 1, in which $R_1$ is methyl or ethyl, $R_2$ is a phenoxy or carbobenzyloxy substituted methyl or ethyl radical, and $R_3$ is selected from the group consisting of hydroxyl and cyanomethyloxy, chloroalkoxy, benzyloxy, or an alkanoyloxymethoxy group, the alkoxy of which has from 1 to 4 carbon atoms, and pharmaceutically acceptable salts thereof.

19. Amidino-penicillanic acid derivatives of formula I of claim 1, in which $R_1$ is methyl or ethyl, $R_2$ is a phenyl or halophenyl substituted methyl or ethyl radical, and $R_3$ is selected from the group consisting of hydroxyl and cyanomethyloxy, chloroalkoxy, benzyloxy, or an alkanoyloxymethoxy group, the alkoxy of which has from 1 to 4 carbon atoms, and pharmaceutically acceptable salts thereof.

20. Amidino-penicillanic acid derivatives of formula I of claim 1, in which $R_1$ is a $C_1$ to $C_4$ alkyl radical, $R_2$ is furylmethyl or furylethyl, and $R_3$ is selected from the group consisting of hydroxyl and cyanomethyloxy, chloroalkoxy, benzyloxy, or an alkanoyloxymethoxy group, the alkoxy of which has from 1 to 4 carbon atoms, and pharmaceutically acceptable salts thereof.

21. Amidino-penicillanic acid derivatives of formula I of claim 1, in which $R_1$ and $R_2$ together with a nitrogen atom forms a heterocyclic radical selected from the group consisting of morpholinyl-4, 4-methylpiperazinyl-1, and 1,2,3,4-tetrahydroisoquinolyl-2, and $R_3$ is selected from the group consisting of hydroxyl and cyanomethyloxy, chloroalkoxy, benzyloxy, or an alkaoyloxymethoxy group, the alkoxy of which has from 1 to 4 carbon atoms, and pharmaceutically acceptble salts thereof.

* * * * *

UNITED STATES PATENT AND TRADEMARK OFFICE

CERTIFICATE EXTENDING PATENT TERM
UNDER 35 U.S.C. 156

Patent No.   : 3,957,764

Dated        : May 18, 1976

Inventor(s)  : Lund

Patent Owner : Lovens Kemiske Fabrik Produktionsaxtieselskab

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

2 YEARS with all rights pertaining thereto as provided by 35 USC 156(b).

I have caused the seal of the Patent and Trademark Office to be affixed this 23rd day of May, 1986.

Donald J. Quigg

Assistant Secretary and Commissioner of Patents and Trademarks